(12) United States Patent
Jeung et al.

(10) Patent No.: US 7,844,094 B2
(45) Date of Patent: Nov. 30, 2010

(54) SYSTEMS AND METHODS FOR DETERMINING GEOMETRIC PARAMETERS OF IMAGING DEVICES

(75) Inventors: Andrew G. Jeung, Mountain View, CA (US); Hassan Mostafavi, Los Altos, CA (US); Alexander Sloutsky, Burlingame, CA (US)

(73) Assignee: Varian Medical Systems, Inc., Palo Alto, CA (US)

( * ) Notice: Subject to any disclaimer, the term of this patent is extended or adjusted under 35 U.S.C. 154(b) by 1216 days.

(21) Appl. No.: 11/119,019

(22) Filed: Apr. 29, 2005

(65) Prior Publication Data

US 2006/0245628 A1 Nov. 2, 2006

(51) Int. Cl.
*G06K 9/00* (2006.01)
(52) U.S. Cl. ..................... 382/131; 382/154
(58) Field of Classification Search ......... 128/897–899; 378/156, 162–164, 20, 87; 382/103, 128, 382/131, 154; 600/415–416, 424
See application file for complete search history.

(56) References Cited

U.S. PATENT DOCUMENTS

| 4,296,329 | A | 10/1981 | Mirabella | 250/491 |
|---|---|---|---|---|
| 6,148,095 | A * | 11/2000 | Prause et al. | 382/131 |
| 6,493,574 | B1 * | 12/2002 | Ehnholm et al. | 600/429 |
| 6,516,046 | B1 * | 2/2003 | Frohlich et al. | 378/65 |
| 6,888,919 | B2 | 5/2005 | Graf | 378/65 |
| 7,065,393 | B2 * | 6/2006 | Sati et al. | 600/407 |
| 2003/0123614 | A1 * | 7/2003 | Silver et al. | 378/146 |
| 2004/0264648 | A1 * | 12/2004 | Claus et al. | 378/163 |
| 2005/0084073 | A1 | 4/2005 | Seppi et al. | 378/156 |
| 2005/0094771 | A1 * | 5/2005 | Basu et al. | 378/207 |
| 2005/0117708 | A1 * | 6/2005 | Cho et al. | 378/164 |
| 2006/0002519 | A1 * | 1/2006 | Jenkins et al. | 378/207 |
| 2006/0245628 | A1 | 11/2006 | Jeung et al. | 382/128 |
| 2007/0041508 | A1 * | 2/2007 | Tubbs | 378/207 |
| 2008/0240535 | A1 * | 10/2008 | Frangioni et al. | 382/131 |

FOREIGN PATENT DOCUMENTS

WO   WO 2005/124296   * 12/2005

OTHER PUBLICATIONS

Rizo, et al. "Geometric Calibration Method for Multiple-Head Cone-Beam SPECT System", IEEE Transactions on Nuclear Science, Dec. 1994 vol. 41, No. 6. pp. 2748-2757.*

Beque et al. "Optimization of Geometrical Calibration in Pinhole SPECT", IEEE Transactions on Medical Imaging vol. 24, No. 2, Feb. 2005 pp. 180-190—device fittings over source beams with geometric parameter calibration.*

(Continued)

*Primary Examiner*—Andrew W Johns
(74) *Attorney, Agent, or Firm*—Vista IP Law Group, LLP.

(57) ABSTRACT

A method of determining a geometric parameter of a machine includes using the machine to obtain an image of at least a portion of a structure, the structure having a plurality of markers, wherein the markers have predetermined position(s) relative to each other, determining a position of the structure based on a pattern of the markers in the image, and determining a geometric parameter of the machine based at least in part on the determined position of the structure.

49 Claims, 13 Drawing Sheets

OTHER PUBLICATIONS

Cho, Y. et al. "Accurate Technique for Complete Geometric Calibration of Cone-Beam Computed Tomography Systems." *Medical Physics* (Apr. 2005) 32(4):968-983.

Fahrig, R. and D.W. Holdsworth "Three-Dimensional Computed Tomographic Reconstruction Using a C-arm Mounted XRII: Image-Based Correction of Gantry Motion Nonidealities" *Medical Physics* (Jan. 2000) 27(1):30-38.

Navab, N. et al. "Dynamic Geometrical Calibration for 3-D Cerebral Angiography." *SPIE* (Feb. 1996) 2705:361-670.

Noo, F. et al. "Analytic Method Based on Identification of Ellipse Parameters for Scanner Calibration in Cone-Beam Tomography." *Phys. Med. Biol.* (2000) 45:3489-3508.

Rougée, A. et al. "Geometrical Calibration for 3D X-ray Imaging." *SPIE* (Sep. 1993) 1897:161-169.

Non-Final Office Action dated Jun. 3, 2010 for U.S. Appl. No. 11/590,075.

Silver et al. "Determination and Correction of the Wobble of a C-arm gantry" Proc. SPIE 3979, 1459-1468 (2000).

Bani-Hashemi et al. "Cone Beam CT Reconstruction with No Isocentricity Requirement" Med. Phys. 30, 1415 (2003).

Navab et al. "Dynamic Geometrical Calibration of 3-D Cerebral Angiography" SPIE (Feb. 1996) 2708: 361-370.

\* cited by examiner

SYSTEMS AND METHODS FOR DETERMINING GEOMETRIC PARAMETERS OF IMAGING DEVICES

BACKGROUND

1. Field of the Invention

This invention relates generally to imaging devices, and more specifically, to systems and methods for determining geometric parameters of imaging devices.

2. Background of the Invention

Computed tomography (CT) is an imaging technique that has been widely used in the medical field. In a procedure for computed tomography, an x-ray source and a detector apparatus are positioned on opposite sides of a portion of a patient under examination. The x-ray source generates and directs an x-ray beam towards the patient, while the detector apparatus measures the x-ray absorption at a plurality of transmission paths defined by the x-ray beam during the process. The detector apparatus produces a voltage proportional to the intensity of incident x-rays, and the voltage is read and digitized for subsequent processing in a computer. By taking hundreds of images from multiple angles around the patient, relatively massive amounts of data are thus accumulated. The accumulated data are then analyzed and processed for reconstruction of a matrix (visual or otherwise), which constitutes a depiction of a density function of the bodily section being examined. By considering one or more of such sections, a skilled diagnostician can often diagnose various bodily ailments such as tumors, blood clots, etc.

Reconstruction of CT images requires an accurate determination of certain geometric parameters of the CT imaging machine, such as the source-to-imager distance (SID), the source-to-axis distance (SAD), the axis of rotation, and/or the piercing point (which is the point of projection of the rotation center onto the imager plane). These parameters are also useful in procedures for localization of anatomical landmarks.

Currently, CT imaging machines are constructed to be as rigid as possible, sometimes with active control mechanisms, with the goal of trying to make at least some of the geometric parameters stay constant during operations of the CT imaging machines. However, despite making the CT imaging machine as rigid as possible, it has been found that certain geometric parameters may still vary as a function of a rotation of the gantry of the CT imaging machine. For example, due to slippage between machine components and/or strains undergone by the components, the radiation source and the imager may move relative to each other. The amount and/or direction of movement between components may vary as the gantry of the CT imaging machine is rotated. Also, due to slippage and strains of machine components, the axis of rotation may be different from what is expected, and/or the piercing point of each image frame may vary as the gantry rotates. Although some geometric parameters can be determined manually by physically measuring them at the CT imaging machine, it would be very difficult and inconvenient to manually obtain geometric parameters for a plurality of prescribed gantry rotational angles.

For the foregoing reason, it would be desirable to have systems and methods for automatically determining geometric parameters of imaging devices.

SUMMARY

In accordance with some embodiments, a system for use in a process to determine one or more geometric parameter(s) of an imaging device includes a calibration device having a plurality of markers. During use, the calibration device is positioned between a radiation source and a detector, and a plurality of images of the calibration device is generated at different gantry angles. The images can be used to determine one or more geometric parameter(s) of the imaging device. In some cases, the system further includes a filter having a characteristic for allowing a center of a radiation source or a center of a radiation beam to be determined. By means of non-limiting examples, the filter can include an opening and/or a plurality of markers.

In accordance with other embodiments, a method of determining a geometric parameter of a machine includes using the machine to obtain an image of at least a portion of a structure, the structure having a plurality of markers, wherein the markers have predetermined position(s) relative to each other, determining a position of the structure based on a pattern of the markers in the image, and determining a geometric parameter of the machine based at least in part on the determined position of the structure.

In accordance with other embodiments, a system for determining a geometric parameter of a machine includes a processor configured to receive an image of at least a portion of a structure, the structure having a plurality of markers, wherein the markers have predetermined position(s) relative to each other, wherein the processor is further configured to determine a position of the structure based on a pattern of the markers in the image, and determine a geometric parameter of the machine based at least in part on the determined position of the structure.

In accordance with other embodiments, a computer program product includes a medium useable by a processor, the medium having a set of instructions, an execution of which causes a process to be performed, the process comprising receiving an image of at least a portion of a structure, the structure having a plurality of markers, wherein the markers have predetermined position(s) relative to each other, determining a position of the structure based on a pattern of the markers in the image, and determining a geometric parameter of a machine based at least in part on the determined position of the structure.

In accordance with other embodiments, a method of determining a geometric parameter of a machine includes using the machine to obtain images of at least a portion of a structure at a plurality of gantry angles, determining positions of the structure relative to a reference frame of the machine based on the obtained images at the plurality of gantry angles, determining a first point on the structure, determining a second point on the structure, and determining an axis of rotation based at least in part on the determined first and second points on the structure.

In accordance with other embodiments, a system for determining a geometric parameter of a machine includes a processor configured to obtain images of at least a portion of a structure at a plurality of gantry angles, wherein the processor is further configured to determine positions of the structure relative to a reference frame of the machine based on the obtained images at the plurality of gantry angles, determine a first point on the structure, determine a second point on the structure, and determine an axis of rotation based at least in part on the determined first and second points on the structure.

In accordance with other embodiments, a computer program product includes a medium useable by a processor, the medium having a set of instructions, an execution of which causes a process to be performed, the process comprising receiving images of at least a portion of a structure at a plurality of gantry angles, determining positions of the structure relative to a reference frame of the machine based on the obtained images at the plurality of gantry angles, determining a first point on the structure, determining a second point on the structure, and determining an axis of rotation based at least in part on the determined first and second points on the structure.

In accordance with other embodiments, a method for use in a system having a machine and a structure being imaged by the machine includes obtaining an image of at least a portion of a structure, the structure having a plurality of markers, wherein the markers have fixed position(s) relative to each other, and determining positions of the markers in the obtained image using a rolling-ball algorithm.

In accordance with other embodiments, a system for use in a system having a machine and a structure being imaged by the machine, includes a processor configured to obtain an image of at least a portion of a structure, the structure having a plurality of markers, wherein the markers have fixed position(s) relative to each other, wherein the processor is further configured to determine positions of the markers in the obtained image using a rolling-ball algorithm.

In accordance with other embodiments, a computer program product includes a medium useable by a processor, the medium having a set of instructions, an execution of which causes a process to be performed, the process comprising obtaining an image of at least a portion of a structure, the structure having a plurality of markers, wherein the markers have fixed position(s) relative to each other, and determining positions of the markers in the obtained image using a rolling-ball algorithm.

In accordance with other embodiments, a method of determining a geometric parameter of a machine includes placing a filter in front of a radiation source, using the machine to obtain a first image at a first gantry angle and a second image at a second gantry angle, determining a first point in a first image that represents the intersection between a center line of a radiation beam at the first gantry angle and a plane of the first image, determining a second point in a second image that represents the intersection between a center line of a radiation beam at the second gantry angle and a plane of the second image, determining a first line that includes the first point, determining a second line that includes the second point, and determining a geometric parameter of the machine based at least in part on the first line and the second line.

In accordance with other embodiments, a system for determining a geometric parameter of a machine includes a filter configured to be secured in front of a radiation source, and a processor, wherein the processor is configured to obtain a first image at a first gantry angle and a second image at a second gantry angle, wherein the first and the second images are generated using the machine, determine a first point in a first image that represents the intersection between a center line of a radiation beam at the first gantry angle and a plane of the first image, determine a second point in a second image that represents the intersection between a center line of a radiation beam at the second gantry angle and a plane of the second image, determine a first line that includes the first point, determining a second line that includes the second point, and determine a geometric parameter of the machine based at least in part on the first line and the second line.

In accordance with other embodiments, a computer program product including a medium useable by a processor, the medium having a set of instructions, an execution of which causes a process to be performed, the process includes obtaining a first image at a first gantry angle and a second image at a second gantry angle, wherein the first and the second images are generated using a radiation source and a filter placed in front of the radiation source, determining a first point in a first image that represents the intersection between a center line of a radiation beam at the first gantry angle and a plane of the first image, determining a second point in a second image that represents the intersection between a center line of a radiation beam at the second gantry angle and a plane of the second image, determining a first line that includes the first point, determining a second line that includes the second point, and determining a geometric parameter of the machine based at least in part on the first line and the second line.

In accordance with other embodiments, a method for use to determine a geometric parameter of a machine includes verifying an isocenter of a machine without placing a marker at the isocenter of the machine.

In accordance with other embodiments, a system for use in a process to determine a geometric parameter of an imaging device includes a structure, and a plurality of markers secured to the structure, wherein the plurality of markers are positioned relative to each such that they collectively form an irregular pattern.

Other aspects and features of the invention will be evident from reading the following detailed description of the preferred embodiments, which are intended to illustrate, not limit, the invention.

BRIEF DESCRIPTION OF THE DRAWINGS

The drawings illustrate the design and utility of preferred embodiments, in which similar elements are referred to by common reference numerals. In order to better appreciate how advantages and objects of the embodiments are obtained, a more particular description of the embodiments will be illustrated in the accompanying drawings.

DETAILED DESCRIPTION OF THE EMBODIMENTS

Figure 1:
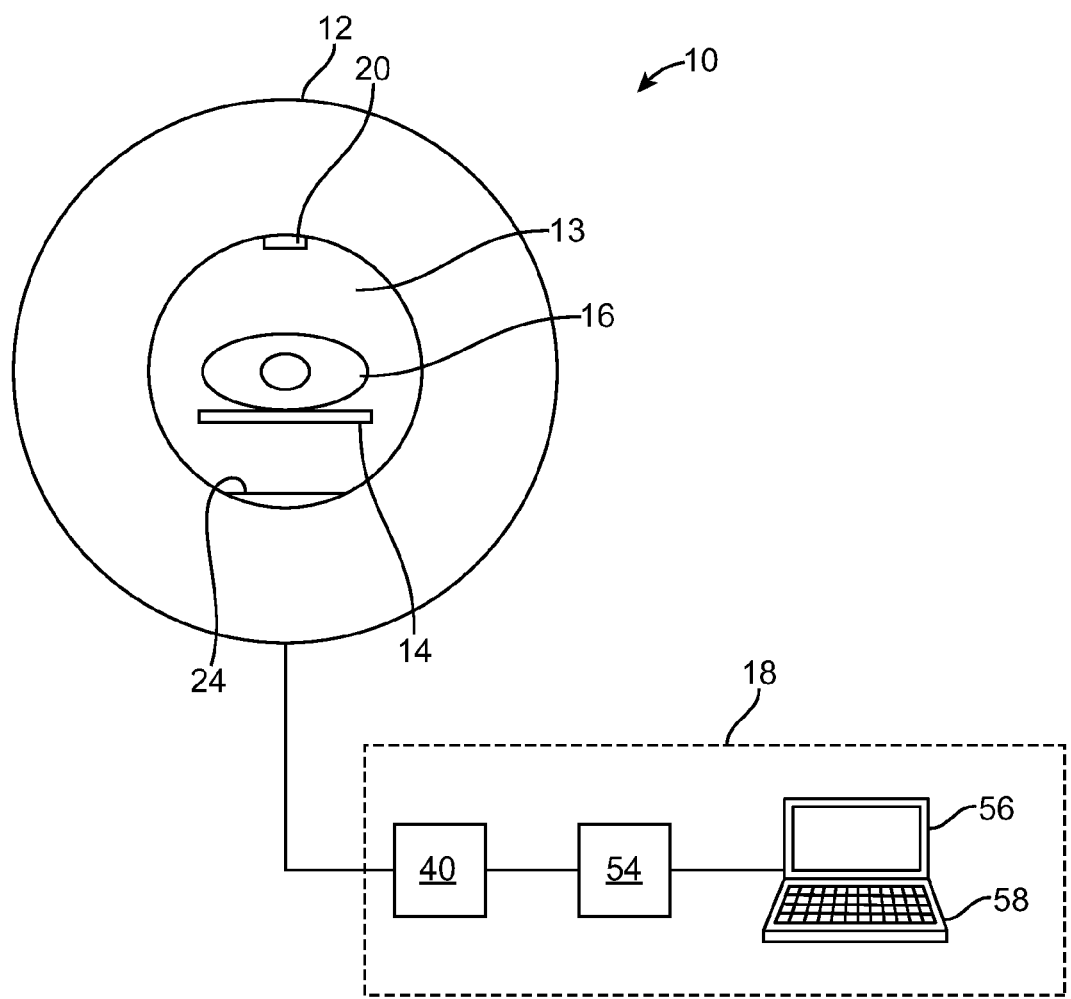
FIG. 1 illustrates a computed tomography system configured to generate images.

Various embodiments are described hereinafter with reference to the figures. It should be noted that the figures are not drawn to scale and elements of similar structures or functions are represented by like reference numerals throughout the figures. It should also be noted that the figures are only intended to facilitate the description of specific embodiments. They are not intended as an exhaustive description of the invention or as a limitation on the scope of the invention. In addition, an aspect described in conjunction with a particular embodiment is not necessarily limited to that embodiment and can be practiced in any other embodiments.

Computed Tomography Image Acquisition System

FIG. 1 illustrates a computed tomography image acquisition system 10. The system 10 includes a gantry 12 having an opening (or bore) 13, a patient support 14 for supporting a patient 16, and a control system 18 for controlling an operation of the gantry 12. In the illustrated embodiments, the gantry 12 has a slip-ring configuration (donut shape). Alternatively, the gantry 12 can have other configurations, such as a C-arm configuration. The system 10 also includes a radiation source (e.g., x-ray source) 20 that projects a beam of radiation towards a detector 24 on an opposite side of the gantry 12 while the patient 16 is positioned at least partially between the radiation source 20 and the detector 24. The radiation source 20 can be configured to generate a cone beam, or alternatively, a fan beam. The detector 24 has a plurality of sensor elements configured for sensing a x-ray that passes through the patient 16. Each sensor element generates an electrical signal representative of an intensity of the x-ray beam as it passes through the patient 16.

The control system 18 includes a processor 54, such as a computer processor, coupled to a gantry rotation control 40. The control system 18 may also include a monitor 56 for displaying data and an input device 58, such as a keyboard or a mouse, for inputting data. During a scan to acquire x-ray projection data (i.e., CT image data), the gantry 12 rotates about the patient 16. The rotation of the gantry 12 and the operation of the radiation source 20 are controlled by the gantry rotation control 40, which provides power and timing signals to the radiation source 20 and controls a rotational speed and position of the gantry 12 based on signals received from the processor 54. Although the control 40 is shown as a separate component from the gantry 12 and the processor 54, in alternative embodiments, the control 40 can be a part of the gantry 12 or the processor 54.

During a radiation procedure, the radiation source 20 generates and directs an x-ray beam towards the patient 16, while the detector 24 measures the x-ray absorption at a plurality of transmission paths defined by the x-ray beam during the process. The detector 24 produces a voltage proportional to the intensity of incident x-rays, and the voltage is read and digitized for subsequent processing in a computer. After image data at different gantry angles have been collected, the collected data are processed for reconstruction of a matrix (CT image), which constitutes a depiction of a density function of the bodily section being examined. By considering one or more of such sections, a skilled diagnostician can often diagnose various bodily ailments. In some cases, the one or more sections can also be used to perform treatment planning.

Calibration Devices

Figure 2:
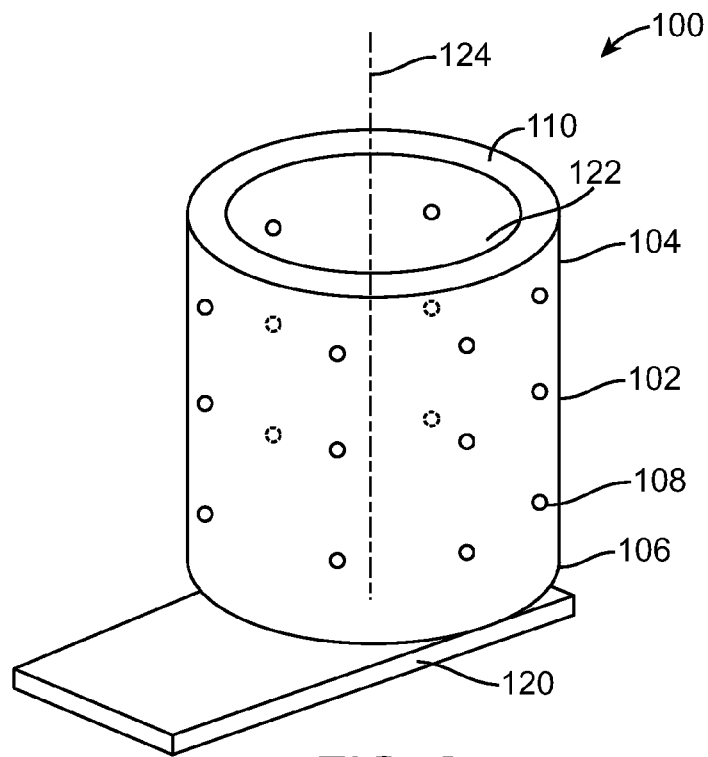
FIG. 2 illustrates a device for use in a procedure to determine geometric parameter(s) of the computed tomography system of FIG. 1 in accordance with some embodiments.

FIG. 2 illustrates a calibration device 100 for use to determine geometric parameter(s) for the system 10. As used in this specification, the term "geometric parameter" refers to a variable associated with an operation of the system 10, such as a position of a component of the system 10, a distance between two components of the system 10, an orientation of a component of the system 10, a source-to-imager distance, a source-to-axis distance, an axis of rotation, a center of rotation, a piercing point, an isocenter (i.e., a point at or adjacent to a location where beams from different gantry angles intersect), and the like. Also, as used in this specification, the term, "imager" is not limited to that used for cone beam CT, and can be any types of imager or detector known in the art of imaging. The device 100 includes a tubular structure 102 having a first end 104 and a second end 106, and a plurality of radio-opaque markers 108 embedded within a wall 110 of the tubular structure 102. In alternative embodiments, instead of a tubular shape, the structure 102 can be a solid object. Also alternatively, instead of embedding the markers 108 within the wall 110, the markers 108 can be secured to a surface (e.g., an interior surface or an exterior surface) of the tubular structure 102. The markers 108 may be permanently secured to the structure 102. In other embodiments, the markers 108 may be detachably secured to the structure 102. For example, each of the markers 108 may have a securing mechanism, such as a Velcro, a pin, a clamp, a screw, a bolt, a clip, or the like, for securing the marker 108 to the structure 102. In some cases, the structure 102 may have a plurality of openings for allowing the markers 108 to be secured to the structure 102.

The tubular structure 102 has a circular cross-sectional shape. In the illustrated embodiments, the tubular structure 102 has a length along its axis that is between 4 and 18 inches, and preferably, 9 inches, and a cross-sectional dimension that is between 4 and 8 inches, and preferably, 9 inches, with the wall having a thickness that is between 0.2 inch to 2 inches, and preferably, 0.5 inch. In other embodiments, the tubular structure 102 can have other cross-sectional shapes (such as an elliptical shape, a square, a rectangular, or other customized shapes) and/or dimensions. In some embodiments, the structure 102 is dimensioned such that its ends 104,106 are not visible in an image frame generated by the system 10.

In the illustrated embodiments, each of the markers 108 is a tungsten-carbide BB (sphere) having a cross-sectional dimension that is between 2 mm to 4 mm. In other embodiments, the markers 108 can be other radio-opaque objects, and can have other cross-sectional dimensions. In further embodiments, the markers 108 are not radio-opaque, but are made from a material that allows them to be distinguishable from the rest of an image. Also, in other embodiments, instead of all the markers 108 having a similar cross-sectional dimension, the markers 108 can have different dimensions. As shown in the figure, the device 100 includes sixteen markers 108. In other embodiments, the device 100 can have fewer or more than sixteen markers 108. For example, the device 100 can have four markers 108 in some embodiments. In some embodiments, the markers 108 are positioned such that as the gantry 12 rotates, all of the markers 108 can be seen in the detector 24 and none of the markers 108 overlap. In the illustrated embodiments, the markers 108 are positioned relative to each other such that they collectively form an irregular pattern. Alternatively, the markers 108 collectively form a regular pattern, such as a spiral, or a portion of a geometric profile. As another example of a regular pattern, a first group of the markers 108 can form a first profile that is a mirror image, or a reverse mirror image, of a second profile formed by a second group of the markers 108.

In the illustrated embodiments, the device 100 further includes a mounting mechanism 120 configured for securing the device 100 to the patient support 14. The mounting mechanism 120 is in a form of a plate which attaches to a set of hooks (not shown) on the patient support 14. Alternatively, the mounting mechanism 120 can have other shapes and/or configurations. Also, in other embodiments, the device 100 does not include the mounting mechanism 120. In such cases, a separate connection may be provided for securing the device 100 relative to the patient support 14.

In the illustrated embodiments, the tubular structure 102 has an unoccupied lumen 122. Alternatively, the lumen 122 can be filled with a material (thereby forming a core) having a density that is different from, or the same as, that of the tubular structure 102. Also, in further embodiments, the device 100 can further include one or more radio-opaque markers embedded within the core material. The marker(s) within the core material may have the same size and shape as those in the wall 110 of the tubular structure 102. Alternatively, the marker(s) within the core material may have size and shape that are different from those in the wall 110 of the tubular structure 102.

Figure 3:
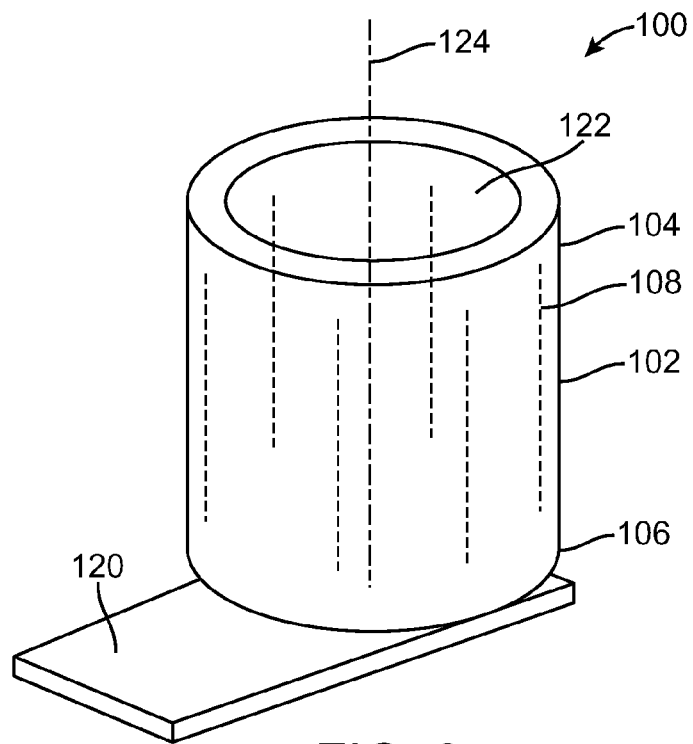
FIG. 3 illustrates a variation of the device of FIG. 2, showing the device having elongated markers.

FIG. 3 illustrates a variation of the device 100 that includes a plurality of elongated markers 108. The elongated markers 108 can be, for example, metal wires. Such configuration is advantageous in that it may be robust against image distortion when the device 100 is being imaged by the system 10. As shown in the figure, the markers 108 have the same length and width, but alternatively, the markers 108 can have different dimensions. Also, instead of the rectilinear profile shown, in other embodiments, the elongated markers 108 can each have a curvilinear or bent profile. In further embodiments, instead of the markers 108 being spaced from each other, one or more of the elongated markers 108 can intersect other marker(s) 108. In addition, in other embodiments, instead of the parallel arrangement shown, the markers 108 may point in different directions.

Geometric Calibration Methods

Figure 4:
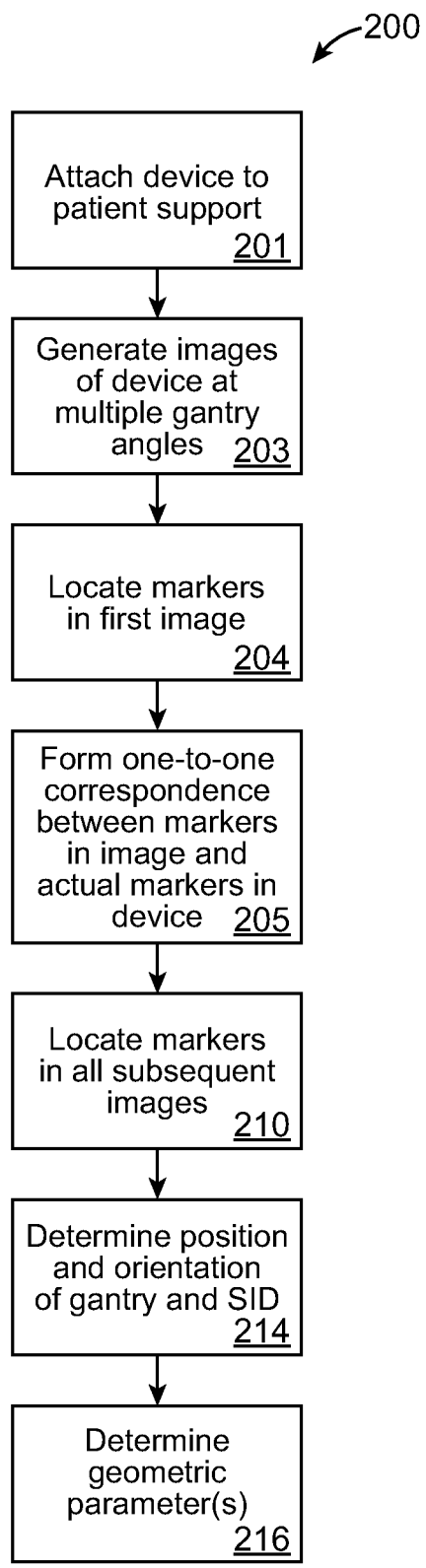
FIG. 4 illustrates a method for determining geometric parameter(s) of the computed tomography system of FIG. 1 in accordance with some embodiments.

FIG. 4 illustrates a method 200 for determining one or more geometric parameters for the system 10. First, the calibration device 100 is secured to the patient support 14 (Step 201). In some embodiments, the device 100 is secured in a known fixed position, and is oriented such that the axis 124 of the device 100 is substantially parallel to (e.g., within 5° from) a rotational axis of the gantry 12. The system 10 is then used to generate a set of images of the device 100 at a plurality of gantry angles (Step 203). In the illustrated embodiments, the gantry 12 is rotated at an increment in the range of ½° to 2° between the acquisition of each image. Alternatively, the gantry 12 can be rotated at other increment of gantry angles. The generated image will include images of the markers 108.

Next, the processor 54 determines the positions of the markers 108 in the first generated image (e.g., the image generated at the first gantry angle) (Step 204). In the illustrated embodiments, the processor 54 is configured (e.g., programmed or designed) to perform a background subtraction of the image frame to remove undesirable background details. For example, a rolling ball technique (commonly used in the field of gel electrophoresis) may be used to perform the background subtraction. In the rolling ball technique, portion(s) of the generated image having a concavity in the grayscale value less than a prescribed threshold is removed. In other embodiments, the process 200 does not include the step of performing background subtraction. After the background subtraction has been performed, the processor 54 then converts the image frame to a binary image by thresholding. The threshold level can be set by calculating the number of pixels expected in the foreground, or by entropy thresholding. The binary image can then be analyzed by the processor 54 to determine the positions of the markers 108 in the generated image. In other embodiments, other techniques known in the art of image processing can also be used to determine the positions of the markers 108 in the generated image.

Next, the processor 54 associates, or forms a one-to-one correspondence, between the projections of each marker 108 in the first generated image and the markers 108 themselves (Step 205). In the illustrated embodiments, the processor 54 forms this correspondence by determining a possible orientation of the device 100 that could produce the arrangement of markers 108 in the image. Various techniques can be employed for such purpose. For example, the processor 54 can be configured to make an initial estimate of the position of the device 100, and then attempt to match at least a subset of the projected positions of the markers 108 (that correspond with the estimated position of the device 100) with at least a subset of the positions of the markers 108 in the actual image. For example, if the generated image contains six markers 108, the processor 54 can be configured to select a subset (e.g., four) of markers 108 in the image, and then attempts to match the four markers 108 with four estimated projected location of the markers 108 that are associated with the estimated position of the device 100. Alternatively, the processor 54 can be configured to use all of the markers 108 in the image to determine a possible orientation of the device 100. In some cases, if an initial estimate of the position of the device 100 cannot be made, an algorithm can be employed in which all possible associations between sets of markers 108 are attempted, with certain obviously incorrect associations eliminated to improve efficiency. Once a match has been found, the estimated position of the device 100 is then determined to be the position of the device 100 at the first gantry angle.

Figure 5:
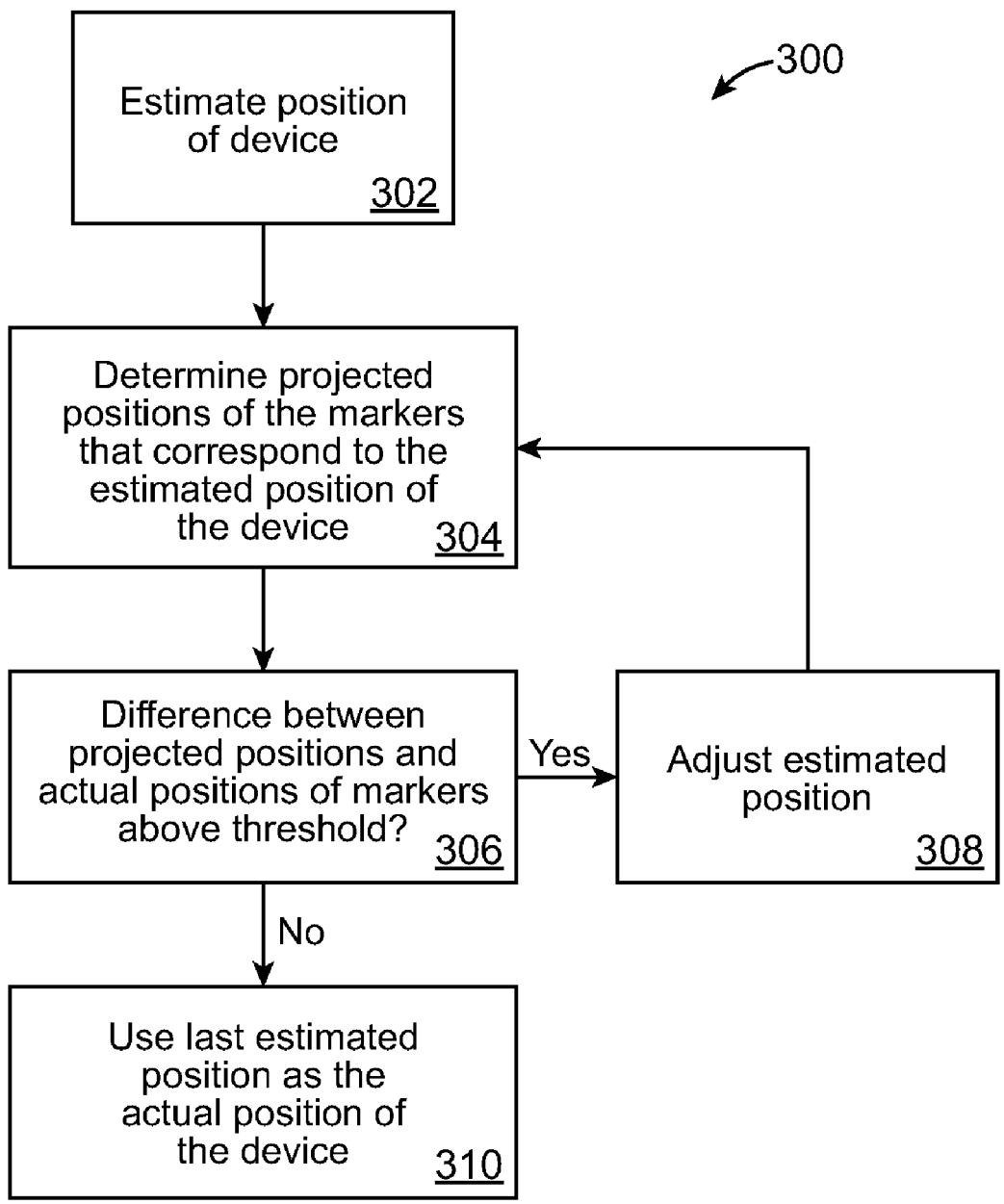
FIG. 5 illustrates a method of optimization in accordance some embodiments.

In some embodiments, an optimization technique can be used to perform optimization of the six degrees of freedom of the device 100 such that the error between the projected positions (associated with the estimate of the device 100 position) and the actual positions of the markers 108 in the image is minimized. FIG. 5 illustrates an optimization technique that can be used in accordance with some embodiments. First, an estimate of a position of the device 100 is determined (e.g., by a random guess) (Step 302). Next, the positions of the markers 108 that correspond with the estimated position of the device 100 are projected onto a plane that coincides with the image plane at the first gantry angle (Step 304). The projected positions are then compared with the actual positions of the markers 108 in the first generated image to determine a difference between the projected positions and the actual positions (Step 306). In some embodiments, the difference can be expressed as a difference vector. If the difference is not within a prescribed threshold, the estimated position of the device 100 is adjusted (Step 308), and steps 304 and 306 are repeated until the difference is within the prescribed threshold. In some embodiments, the adjusting is performed using a Gauss method by computing an inverse Jacobian matrix of marker positions. If the difference between the projected positions and the actual positions of the markers 108 is within the prescribed threshold, the last estimated position of the device 100 is then determined to be the position of the device 100 at the first gantry angle (Step 310). A process for determining the six degrees of freedom of an object is disclosed in U.S. patent application Ser. No. 10/234,658, filed Sep. 3, 2002, which is hereby incorporated by reference in its entirety.

If the above-described automatic correspondence schemes fail, a manual correspondence can be performed in which a user establishes the position of the device 100 graphically.

In some embodiments, the device 100 can be designed to have a certain size, and the number and distribution of markers 108 can be selected such that the processor 54 can determine the position of the device 100 even if a portion of the device 100 is outside the image frame. This can be accomplished as long as a subset (e.g., at least four, and preferably, six) of the markers 108 can be detected in the image frame, thereby allowing the processor 54 to determine a position of the device 100 by associating the subset of markers 108 with a possible orientation of the device 100.

Returning to FIG. 4, next, the processor 54 determines the positions of the markers 108 in all subsequent images in the set generated in step 203 (Step 210). In the illustrated embodiments, the initial determined position of the device 100 at the first gantry angle can be used to assist determination of the positions of the markers 108 in the rest of the image frames generated at other gantry angles. For example, the estimated positions of the device 100 for the rest of the gantry angles can be calculated using the initial determined position of the device 100 and the incremental gantry angle (e.g., by rotating the device 100 from the first determined position through a prescribed gantry angle, and calculating the position of the rotated device 100). Using the estimated positions of the device 100 at the gantry angles, the processor 54 can then be configured to determine the expected positions of the markers 108 in the rest of the generated images (e.g., by performing mathematical projections). In such cases, the processor 54 can perform background subtraction and/or cross-correlation on a small region around each of the expected positions of the markers 108 in the image. Such technique has the advantage of making the process more efficient. Also, in some embodiments, the location of each of the markers 108 can be determined by cross-correlation of each image with a convolution kernel of the marker 108. The kernel is generated by creating a map of expected relative x-ray transmission through a marker 108 of expected size. In other embodiments, the positions of the markers 108 in the image frames can be determined using other image processing techniques. For example, the processor 54 can be configured to perform a full inspection of each of the image frames to determine the positions of the markers 108 in each image.

In some embodiments, after the positions of the markers 108 at all prescribed gantry angles have been obtained, the processor 54 then determines the actual position of the gantry 12 at each of the prescribed gantry angles, as well as the distance between the radiation source 20 and the detector 24 (also known as the source-to-imager distance, or SID) (Step 214).

Figure 6:
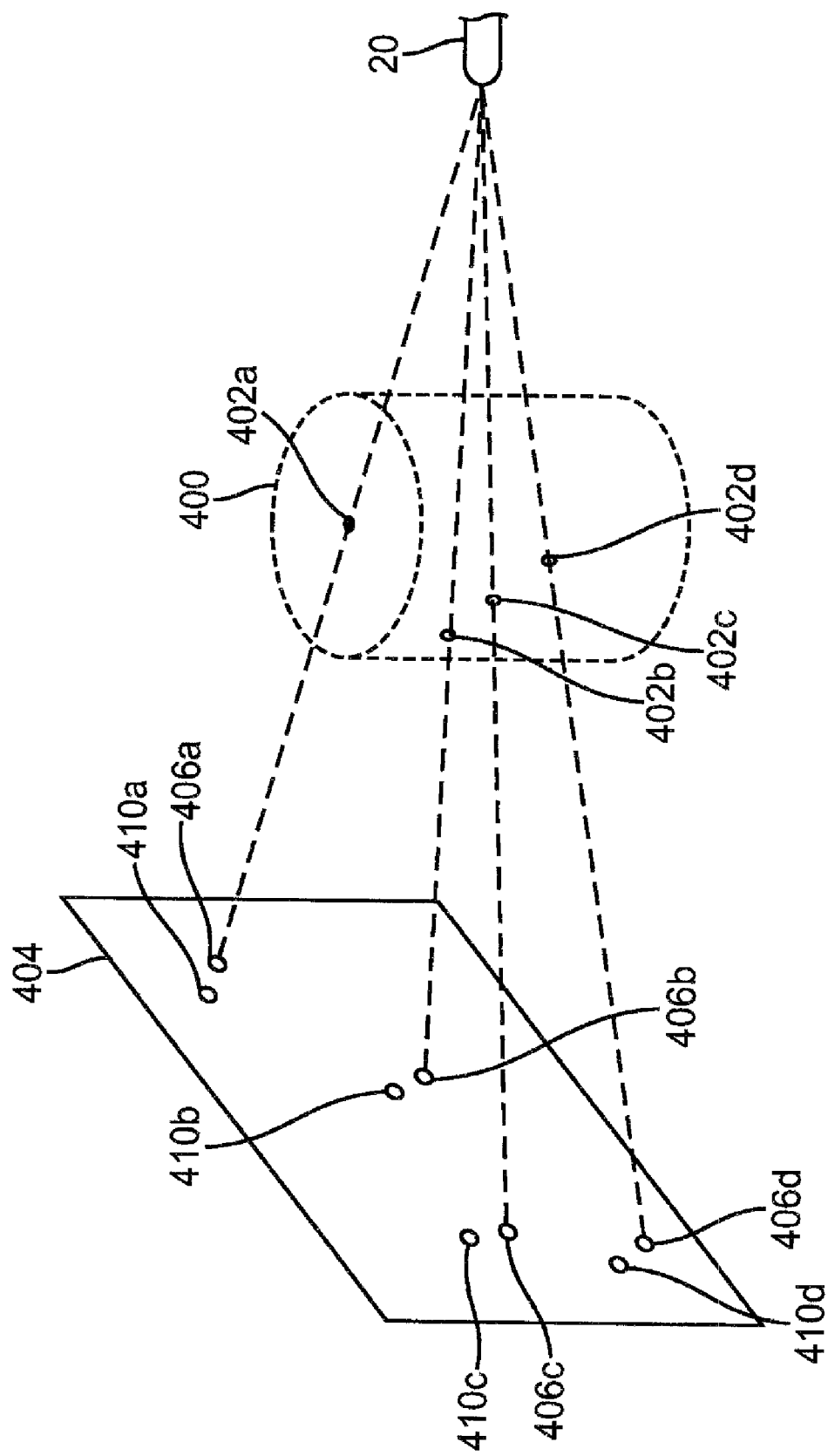
FIG. 6 is a diagram illustrating an example of correlating estimated marker positions with actual marker positions.

Various techniques can be used for such purpose. In the illustrated embodiments, the processor 54 creates an initial estimate of the gantry's six degrees of freedom (i.e., x-coordinate, y-coordinate, z-coordinate, roll, pitch, yaw) plus the SID. The initial estimate can be determined from the known nominal positions of the radiation source 20 and the detector 24 at the prescribed gantry angle, by using the processor 54 to provide a random guess, or alternatively, by a user who input the estimate into the processor 54. The processor 54 then determines projected positions of the markers 108,(in the plane of the detector 24) that correspond to the estimated position of the gantry. FIG. 6 illustrates an example of such step. As shown in FIG. 6, dotted line 400 represents the fixed position of the device 100 relative to the estimated position of the gantry 12, and points 402 represents the relative positions of the markers 108 that correspond with this estimated position of the gantry 12. The processor 54 projects the position of the markers 108 onto image frame 404. The projected positions are represented as points 406 in the figure.

Next, the processor 54 compares the projected positions of the markers 108 (e.g., positions of points 406 in the above example) with the actual positions of the markers 108 in the image frame (e.g., positions of points 410 in FIG. 6). In some embodiments, if the difference between the projected positions and the actual positions of the markers 108 is above a prescribed threshold, the processor 54 then adjusts the estimate of the position and SID of the gantry 12. The amount and direction of adjustment for the estimated position can be determined based on the difference between each of the projected positions and each of the actual positions of the markers 108. This adjustment can be computed using the Gauss method from the inverse Jacobian matrix of marker positions as a function of the seven degrees of freedom of gantry position plus SID. The step of adjusting the estimate and the step of projecting marker positions are repeated until the difference between the projected positions and the actual positions of the markers 108 is at or below the prescribed threshold. Once it is determined that the difference between the projected positions and the actual positions of the markers 108 is at or below the prescribed threshold, the processor 54 then uses the last estimated position and SID of the gantry 12 as the actual position and the actual SID of the gantry 12. This technique is similar to that discussed previously with reference to FIG. 5, except that seven degrees of freedom (six position and orientation plus the SID) are being optimized. In some embodiments, after the seven degrees of freedom are optimized for each gantry angle, an average SID can be determined by taking an average of all the SID values. This average SID can then be used as a fixed value in a second optimization procedure, in which the six positional degrees of freedom of the gantry 12 are optimized. This dual optimization scheme reduces instability in the optimization due to difficulty in accurately determining the SID in any single image.

Figure 7:
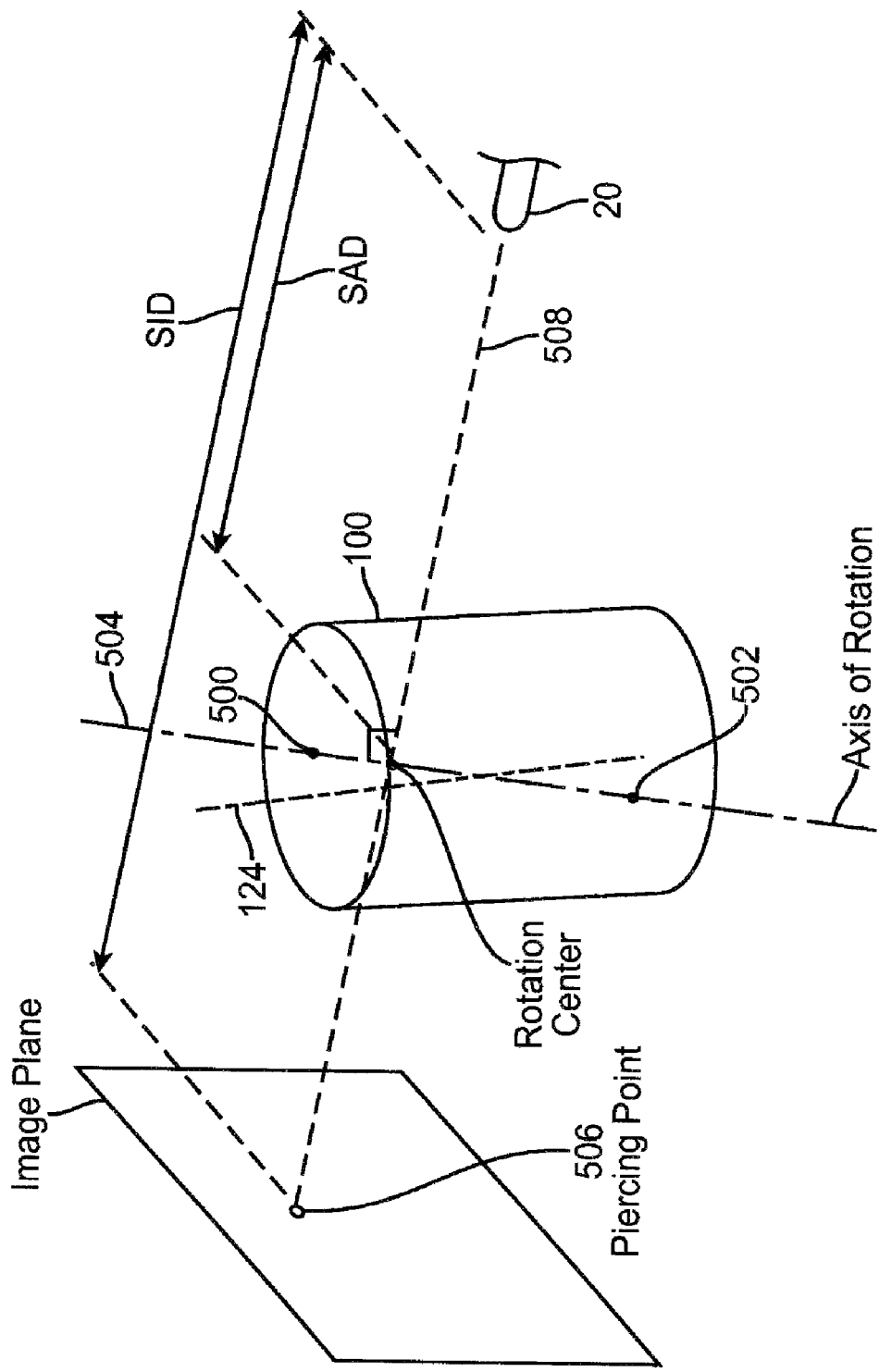
FIG. 7 is a diagram illustrating geometric parameters that can be determined using the method of FIG. 4.

Returning to FIG. 4, after the positions of the gantry 12 at all prescribed gantry angles have been determined, the processor 54 determines one or more geometric parameters based on the determined positions of the gantry 12 (Step 216). FIG. 7 is a diagram illustrating examples of different geometric parameters that can be determined by the processor 54. This diagram is drawn in the reference frame of the gantry 12, and as the gantry 12 rotates, the device 100 appears to be rotating. In the illustrated embodiments, the processor 54 determines a first point 500 and a second point 502 on the device 100 that are relatively fixed (i.e., with no or little sinusoidal motion) with respect to the rest of the structure 100 in the reference frame of the gantry 12. The processor 54 then determines an axis of rotation 504 by determining a line that connects the first and the second points 500, 502. Note that the axis of rotation 504 may or may not coincide, or be parallel, with the axis 124 of the device 100. In some embodiments, the processor 54 can determine the rotation center for the system 10. The rotation center is obtained by determining a line 508 that is perpendicular to the axis of rotation, wherein the line coincides with the radiation source 20 (or a focal point of the radiation source 20) of the system 10. The intersection of the line 508 and the axis of rotation 504 defines the rotation center. In some embodiments, the source-to-axis distance (also known as SAD) can be determined as the distance between the radiation source 20 and the rotation center. In some embodiments, the processor 54 can further determine a piercing point 506 for each of the prescribed gantry angles. The point of intersection between the line 508 and the plane of the detector 24 at a prescribed gantry angle is the piercing point 506 for that gantry angle. As shown in the above example, the device 100 and the processor 54 are advantageous in that they allow various geometric parameters associated with the system 10 be determined automatically, and in an efficient and accurate manner. Using the device 100 and the processor 54 to determine a plurality of geometric parameters is also advantageous because they eliminate the need to use different devices to measure different geometric parameters of the system 10.

Those skilled in the art understand that the various geometric parameters described herein can be used in different applications. For example, the SID, SAD, and piercing point information can be used as parameters for cone beam CT reconstructions. The rotation center can be used to calibrate alignment lasers associated with the system 10, and/or to corroborate alignment of dual-plane imaging systems. Also, the actual gantry angle can be compared to the nominal gantry angle for each frame to investigate slippage in the gantry drive.

Although particular embodiments of the method 200 has been described, the scope of the invention should not be so limited. In other embodiments, the method 200 does not include all of the steps. For example, in other embodiments, the method 200 does not include the step 214 and/or 216. Also, in other embodiments, the order of the steps in the method 200 can be different from that described previously. In addition, in other embodiments, one or more steps in the method 200 can be further divided into sub-steps. In further embodiments, one or more steps in the method 200 can be combined with other step(s).

Figure 8:
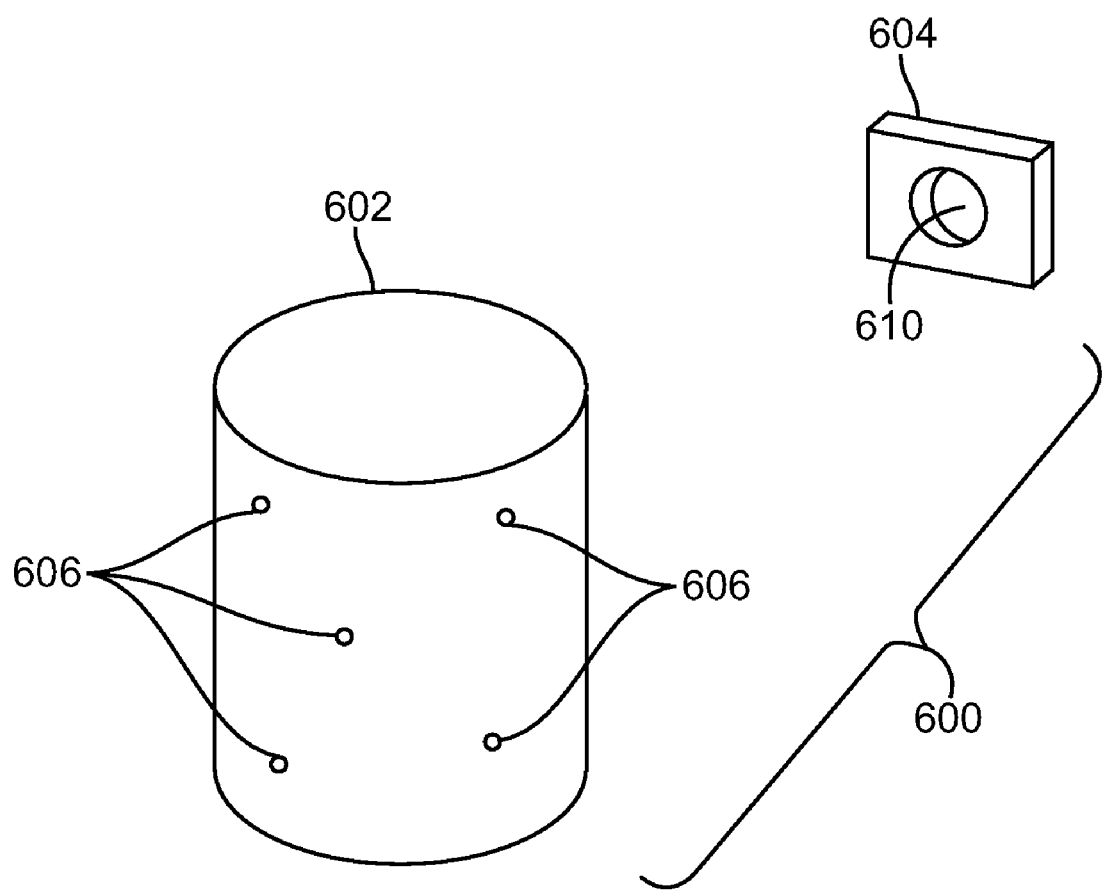
FIG. 8 illustrates a system for use in a procedure to determine geometric parameter(s) of the computed tomography system of FIG. 1 in accordance with some embodiments.

FIG. 8 illustrates a calibration system 600 for use to determine geometric parameter(s) for the system 10 in accordance with other embodiments. The system 600 includes a calibration device 602 and a filter 604. The calibration device 602 can be any of the calibration devices 100 described herein, and includes a plurality of markers 606 as similarly discussed previously. The filter 604 is made from a material that allows the filter 604 to block some of the radiation generated by the radiation source 20, and includes an opening 610 for allowing some of the radiation to pass therethrough. The filter 604 is configured to be secured between the radiation source 20 and the calibration device 602 during use. For example, the filter 604 can include a portion, e.g., a surface or a connection, that allows the filter 604 to be secured in front of the radiation source 20. In the illustrated embodiments, the opening 610 of the filter 604 has a circular shape. Alternatively, the opening 610 can have other shapes, such as a triangle, a square, a rectangle, an ellipse, or a customized shape. Also, instead of having the planar configuration shown, the filter 604 can have other configurations in other embodiments. For example, the filter 604 can have a shape of a block, or a shape of a tube.

Figure 9:
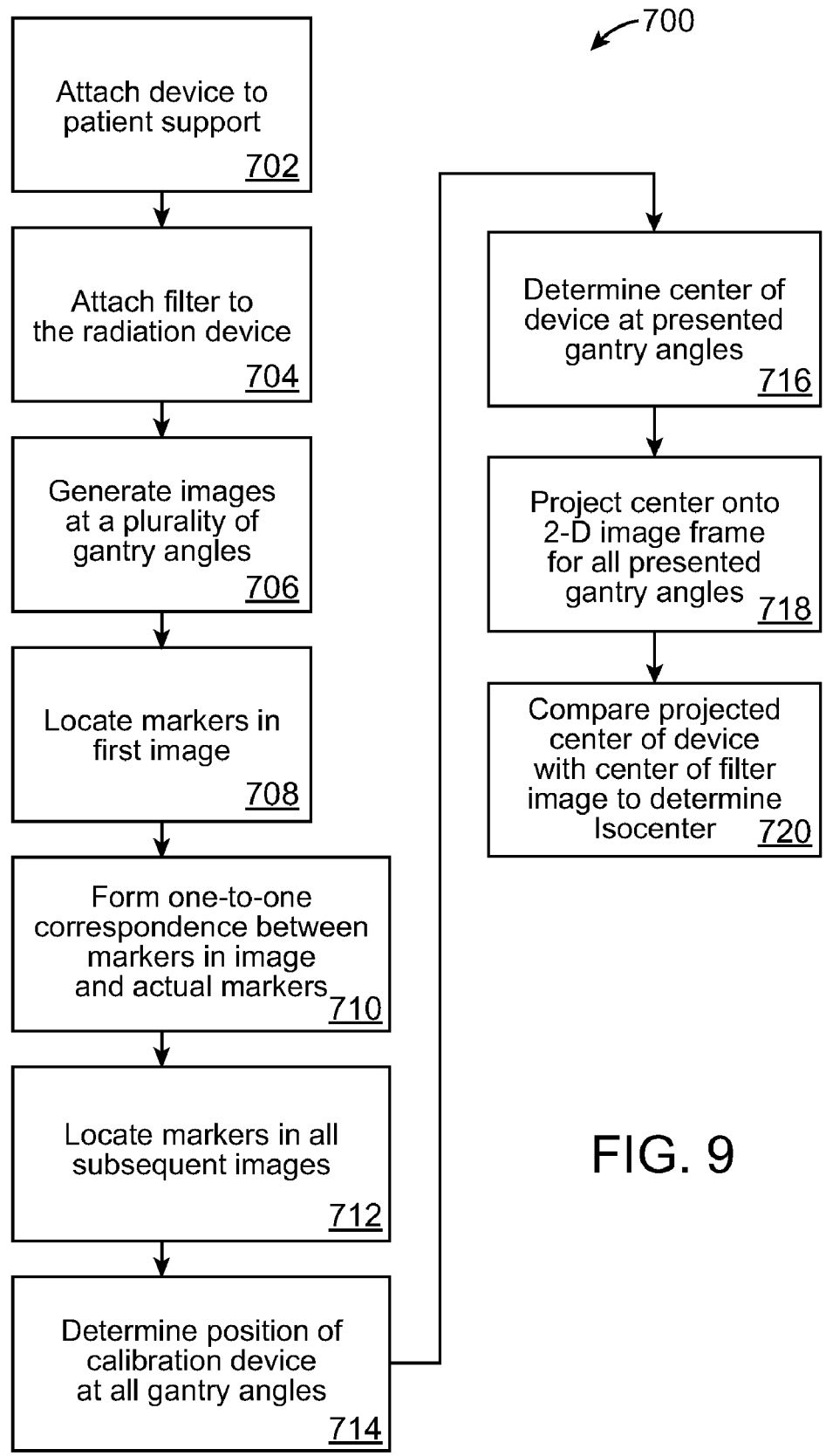
FIG. 9 illustrates a method for determining geometric parameter(s) of the computed tomography system of FIG. 1 using the system of FIG. 8 in accordance with some embodiments.

In some embodiments, the calibration system 600 can be used to determine an isocenter of the system 10. FIG. 9 illustrates a method 700 for determining an isocenter of the system 10 in accordance with some embodiments. First, the calibration device 602 is secured to the system 10 such that a geometric center of the calibration device 602 is located at, or coincides with, an expected/estimated isocenter position of the system 10 (Step 702). The filter 604 is then secured between the radiation source 20 and the calibration device 602 (Step 704). In one implementation, the filter 604 is secured in front of the radiation source 20.

Figure 10:
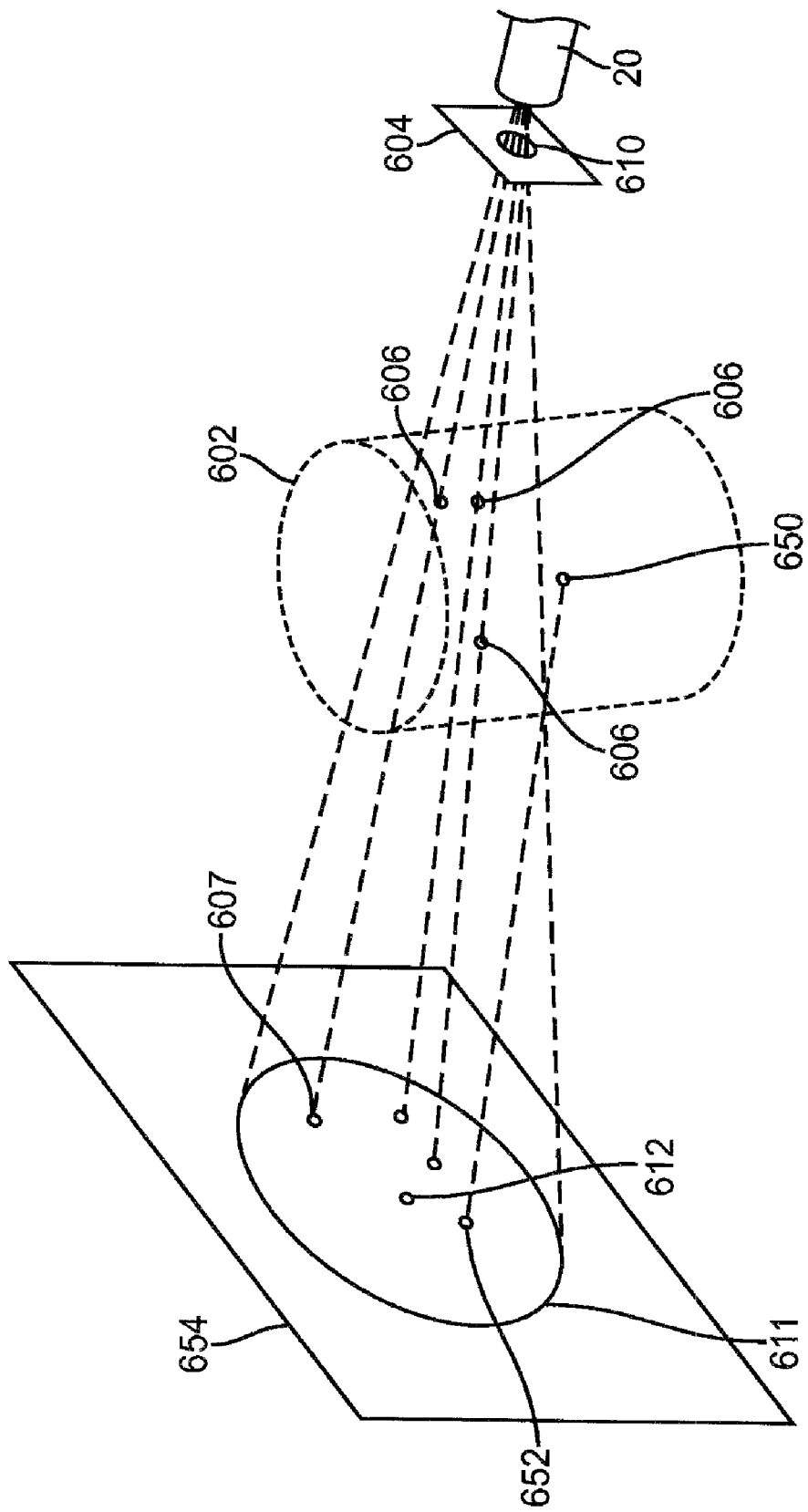
FIG. 10 is a diagram illustrating an example of an image of a filter opening.

Next, the system 10 is used to generate images at a plurality of gantry angles (Step 706). This step is similar to step 203 of FIG. 4. Because the opening 610 of the filter 604 allows a portion of the generated radiation to pass therethrough, the generated images will each have an image of the filter opening 610. For the case in which the opening 610 is circular, each of the generated images will have an image 611 that corresponds with the opening 610 of the filter 604 (FIG. 10). In the illustrated embodiments, because the filter opening 610 is circular, the image 611 is also circular, with a center 612 of the image 611 indicating a center of a radiation beam (or a center of the radiation source 20).

Next, the processor 54 determines the positions of the markers 606 in the first generated image (e.g., the image generated at the first gantry angle) (Step 708), forms a one-to-one correspondence between the projections of each marker 606 in the first generated image and the markers 606 themselves (Step 710), and determines the positions of the markers 606 in all subsequent images in the set generated in step 706 (Step 712). Steps 708, 710, and 712 are similar to steps 204, 205, and 210 of FIG. 4. As shown in FIG. 10, because the projection image 611 of the filter opening 610 is larger than an image 607 of each of the markers 606, and because the projection image 611 will appear brighter than the marker images 607, the projection image 611 (and therefore, the center of the radiation source 20) can be determined by the processor 54 without interfering with a tracking of the markers 606.

Next, based on the determined positions of the markers 606, the position of the device 602 at each of the prescribed gantry angles is determined (Step 714). Similar techniques described with reference to the method 200 of FIG. 4 can be used for such purpose. 070 Next, at each prescribed gantry angle, the coordinate of the geometric center 650 of the device 602 can be determined using the determined position of the device 602 (Step 716). In one implementation, because the center 650 relative to a local reference frame of the device 602 is known, such information can be used to calculate the-coordinate of the center 650 based on the determined position of the device 602. In some cases, if the position of the device 602 is calculated or expressed in step 714 as the coordinate of the center 650 of the device 602, then step 716 is not required.

After the coordinate of the geometric center 650 of the device 602 has been determined, the geometric center 650 is then projected (e.g., by performing a mathematical projection) onto a two-dimensional image frame for each of the prescribed gantry angles (Step 718). FIG. 10 illustrates the center 650 of the device 602 and its projected image 652 in the two-dimensional image frame 654 that corresponds with the detector position.

Next, the projected position of the center of the device 602 is compared with the center 612 of the projected circle 611 in the image for each of the prescribed gantry angles to determine/verify the actual isocenter (Step 720). In one implementation, if the projected position of the center of the device 602 is at, or is within a prescribed distance from, the center 612 of the projected circle 611 in at least two of the generated images, then the initial expected isocenter is determined to be the actual isocenter of the system 10. If the projected position of the center of the device 602 is not at, or is beyond a prescribed distance from, the center 612 of the projected circle 611 in one or more of the generated images, then the initial expected isocenter position can be adjusted (e.g., based on the difference between the projected position of the center of the device 602 and the center 612 of the projected circle 611), and steps 702 and 706-720 are repeated until the projected position of the center of the device 602 is at, or is within a prescribed distance from, the center 612 of the projected circle 611 in at least two of the generated images. In other embodiments, if more than two images are generated, the expected isocenter position can be adjusted until the difference between the projected position of the center of the device 602 and the center 612 of the projected circle 611 for each of the generated images is optimized (e.g., minimized). For example, such optimization can be performed by calculating the some of the differences, or the some of the square of the differences, between the projected position of the center of the device 602 and the center 612 of the projected circle 611 for all of the generated images.

In some embodiments, before or after the isocenter of the system 10 is determined, the processor 54 can also determine the position and orientation of the gantry 12 and SID (as similarly discussed with reference to step 214 of FIG. 4), and other geometric parameter(s) for the system 10 (as similarly discussed with reference to step 216 of FIG. 4).

As illustrated in the above embodiments, the calibration system 600 is advantageous because the same calibration device 602 that is used to determine a rotation center of the system 10 can also be used to determine an isocenter of the system 10. In addition, determining the isocenter of the system 10 using the calibration system 600 does not require placing a marker at the expected isocenter.

In the above embodiments, the calibration device 602 is secured relative to the system 10 such that its geometric center coincides with an expected isocenter of the system 10. However, such needs not be the case. In alternative embodiments, the calibration device 602 can be secured relative to the system 10 such that a prescribed point associated with the calibration device 602, which may or may not be the geometric center of the calibration device 602, coincides with the expected isocenter of the system 10. Before use, the position of the prescribed point relative to a local coordinate of the device 602 is determined. The method 700 of FIG. 9 can then be similarly performed using such a device 602. However, in step 716, instead of determining the center of the device 602, the prescribed point of the device 602 is determined for each prescribed gantry angle, and in step 718, the determined prescribed point is then projected onto the two-dimensional image frame. Also, in step 720, instead of comparing the projected center of the device 602 with the center 612 of the filter opening image 611, the projected prescribed point is compared with the center 612 of the filter opening image 611 to determine the isocenter of the system 10.

Figure 11:
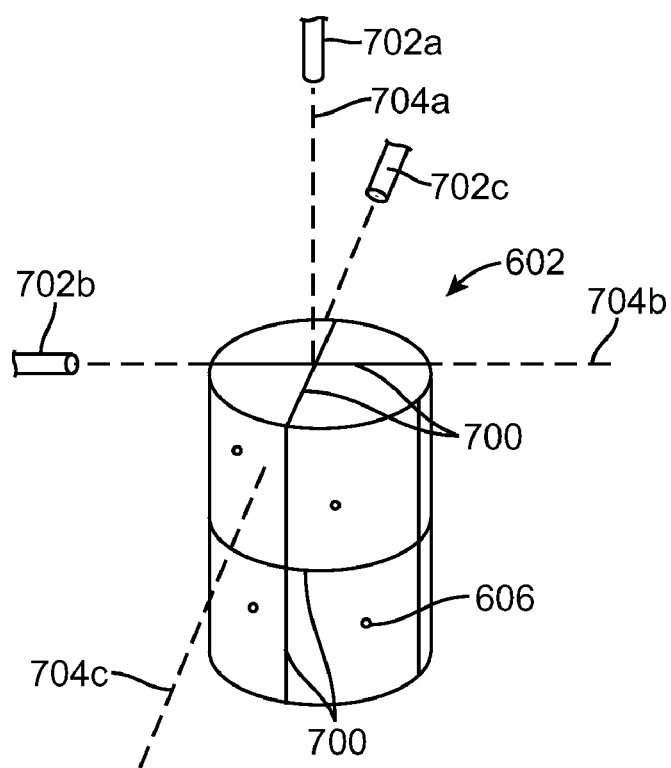
FIG. 11 illustrates a calibration device having a plurality of markings for aligning the calibration device with the system of FIG. 1 in accordance with some embodiments.

In any of the embodiments described herein, the calibration device 602 (or 100) can further include one or more alignment markings for assisting positioning the calibration device 602 relative to the system 10. FIG. 11 illustrates a variation of the calibration device 602, which further includes a plurality of alignment markings 700. In the illustrated embodiments, the alignment markings 700 are orthogonal relative to each other. Alternatively, the alignment markings 700 can have other configurations (size, shape, and/or orientation). When securing the device 602 relative to the system 10, the position of the device 602 is adjusted until the alignment markings 700 align with alignment laser beams 704a-c generated by laser devices 702a-c that are secured to the system 10.

Figure 12:
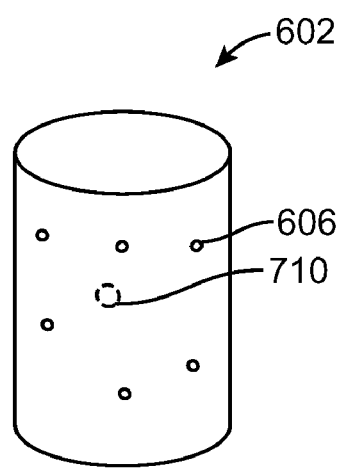
FIG. 12 illustrates a calibration device having an isocenter marker in accordance with some embodiments.

In other embodiments, the calibration device 602 can further include an isocenter marker 710 (FIG. 12). The isocenter marker 710 can have a different shape and/or size from that of the markers 606. In the illustrated embodiments, the isocenter marker 710 is secured at or adjacent to a center of the calibration device 602. In other embodiments, the isocenter marker 710 can be secured to other locations on/in the device 602. During use, the calibration device 602 is secured relative to the system 10 such that the isocenter marker 710 coincides with an expected isocenter of the-system 10. In some embodiments, the device 602 can further include alignment markings, such as those described with reference to FIG. 11, to assist positioning of the device 602 relative to the system 10. Next, the filter 604 is secured in front of the radiation source 20, and the system 10 is used to generate a plurality of images at different gantry angles. These steps are similar to steps 704 and 706 of the method 700. Next, the processor 54 determines the position of the device 602 at each of the prescribed gantry angles (e.g., by performing steps 708-714), and determines one or more geometric parameter of the system 10 (e.g., by performing step 214 and/or 216).

In the illustrated embodiments, the isocenter of the system 10 is also determined/verified. In such cases, each of the generated images will also include an image of the isocenter marker 710. As such, steps 716 and 718 need not be performed, and the image of the isocenter marker 710 can be compared with the center 612 of the filter opening image 611 to determine if the expected isocenter coincides with the actual isocenter (as represented by the center 612) of the system 10. In some embodiments, if the image of the isocenter marker 710 coincides with the center 612 of the filter opening image 611 in at least two image frames, the expected isocenter is then determined to be the actual isocenter of the system 10.

Figure 13:
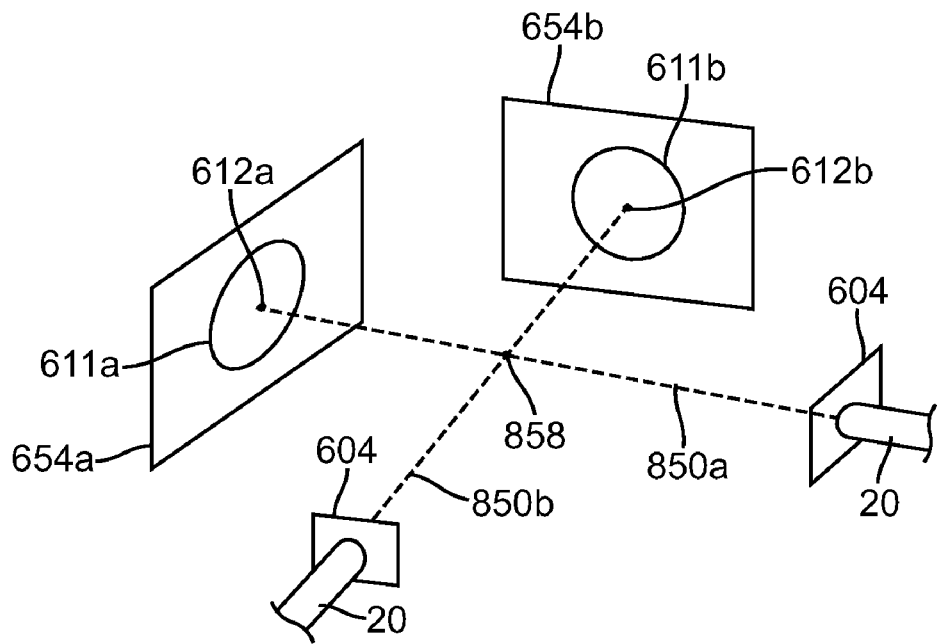
FIG. 13 illustrates a method of determining an isocenter in accordance with some embodiments.
Figure 14:
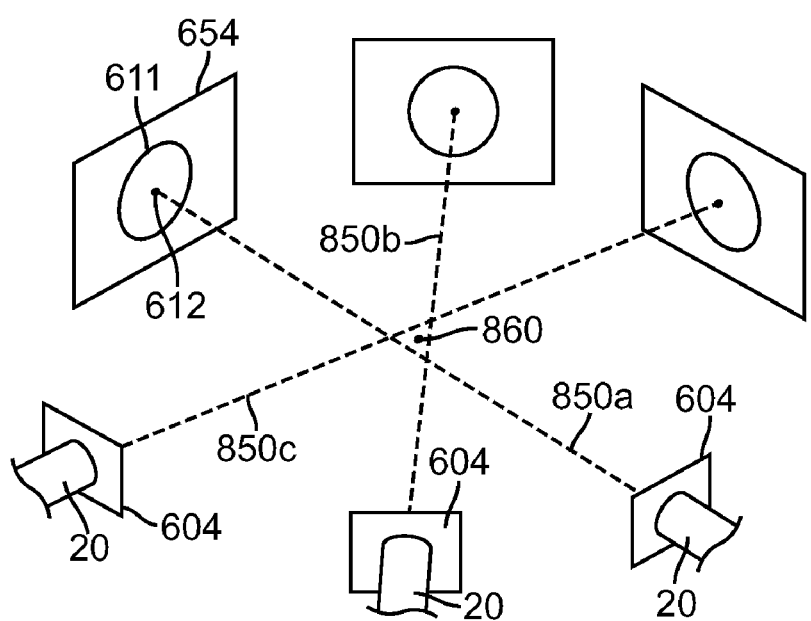
FIG. 14 illustrates a method of determining an isocenter in accordance with other embodiments.
Figure 15:
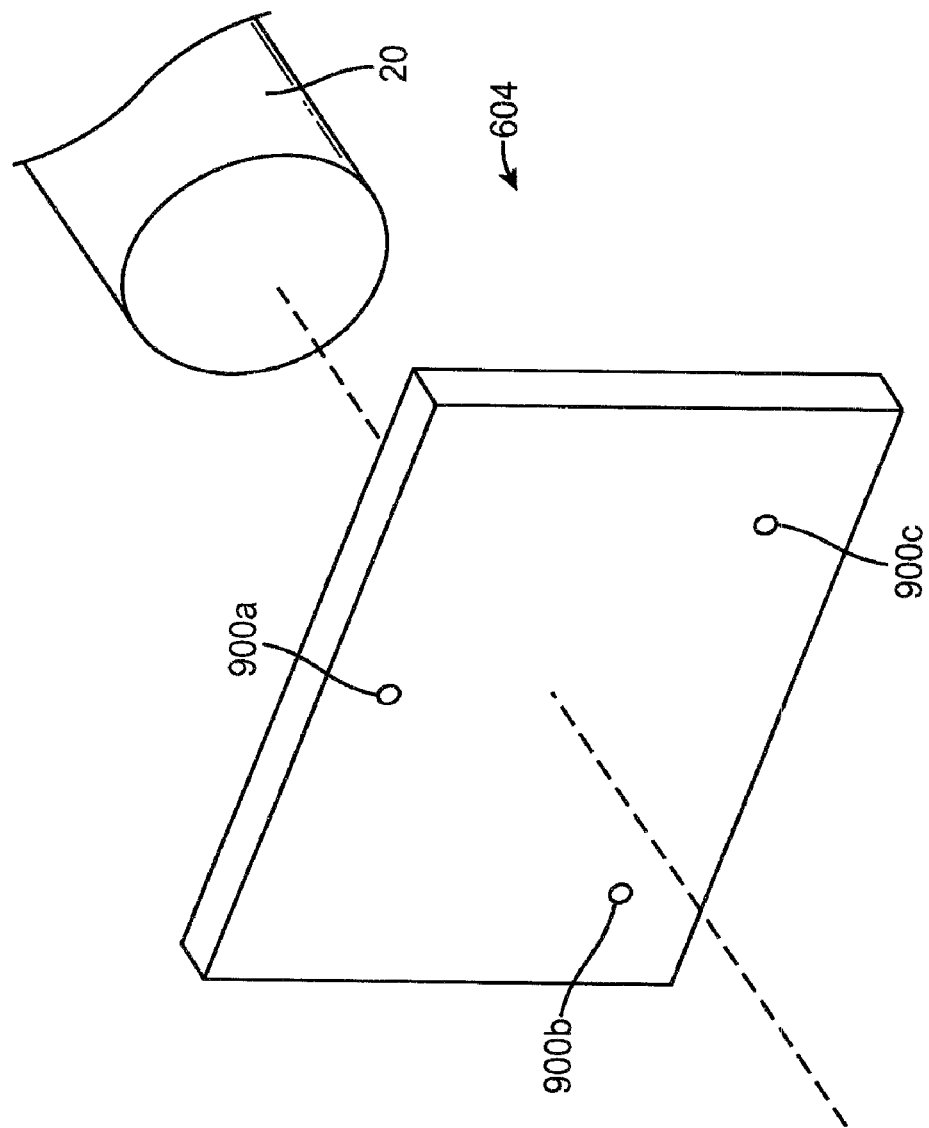
FIG. 15 illustrates a filter in accordance with some embodiments.

In the above embodiments, the calibration system 600 includes both the calibration device 602 and the filter 604. In alternative embodiments, the calibration system 600 does not include the calibration device 602. In such cases, the filter 604 can be attached to the system 10, and the isocenter of the system 10 can be determined without use of a calibration device. For example, the positions of the detector 24 at all prescribed gantry positions (e.g., two gantry positions) can first be determined. Such can be accomplished by physically measuring the positions of the detector 24 at the prescribed gantry positions. Alternatively, such can be accomplished by performing the process 200, or using any of the conventional techniques known in the art. Then, the filter 604 is attached to the system 10, and the system 10 can be used to generate a plurality of images. In such cases, instead of comparing the projection of a center of a calibration device to the center 612 of the projected filter opening image 611 in each of the generated images to see if they coincide, the processor 54 takes the center 612 of the circular opening image 611 in each of the generated image to be the projection of the actual isocenter. In some embodiments, the processor 54 determines a first line 850a between a center 612a of a filter opening image 611a in a first image 654a and a center of the radiation source 20 at a first gantry angle, and a second line 850b between a center 612b of a filter opening image 611b in a second image 654b and a center of the radiation source 20 at a second gantry angle, and then calculates the intersection 858 between the first and the second lines 850a, 850b (FIG. 13). The processor 54 then uses the intersection 858 as the actual isocenter of the system 10. Alternatively, the processor 54 can determine more than two lines 850 (e.g., three lines 850a-c), each of which being a line that is between a center 612 of a filter opening image 611 in an image 654 and a center of the radiation source 20 at a prescribed gantry angle. In such cases, the processor 54 determines a best-fit point 860, and uses the coordinate of the point 860 as the actual isocenter position of the system 10 (FIG. 14). In other embodiments, instead of using center 612 of a filter opening image 611 for processing, the processor 54 can use another variable or attribute associated with a configuration of the filter opening image 611 for processing. 080 In the above embodiments, the filter 604 includes the opening 610. In other embodiments, the filter 604 does not include the opening 610. FIG. 15 illustrates a variation of the filter 604. In FIG. 15, the filter 604 is made from a material (e.g., a transparent material) that allows at least some or all of the radiation generated by the radiation source 20 to pass therethrough. In some embodiments, instead of the planar configuration shown, the filter 604,can have other configurations. For example, the filter 604 can have a shape that resembles a block or a tube. In the illustrated embodiments, the filter 604 includes three markers 900a-c for indicating a center of the radiation source 20. Particularly, the three markers 900a-c are positioned such that their centroid position corresponds with the center of the radiation source 20. Alternatively, the filter 604 can include more than three markers 900 (e.g., four markers). In such cases, the four markers can be positioned at or adjacent to four corners of the filter 604, with the centroid position of the four markers corresponding to a center of the radiation source 20. When using the filter 604 of FIG. 15 to determine an isocenter of the system 10, the method 700 of FIG. 9 is used, with the exception that instead of using a center 612 of a filter opening image 611 in an image frame for analysis or processing, the centroid position of the filter markers 900 as they appear in the image frame is used. In some embodiments, the filter marker 900 can have a different shape and/or size from that of the device marker 606 in order to allow the filter marker 900 to be distinguishable from the device marker 606 in an image. Also, in other embodiments, instead of using centroid position of the markers 900 to indicate the center of the radiation source 20, another variable or attribute associated with the configuration of the markers 900 can be used to indicate the center of the radiation source 20.

It should be noted that the filter 604 of the calibration system 600 should not be limited to the examples discussed previously, and that the filter 604 can also have other configurations, as long as the filter 604 has a characteristic for allowing a center of a radiation source, or a center of a radiation beam, to be determined.

Computer System Architecture

Figure 16:
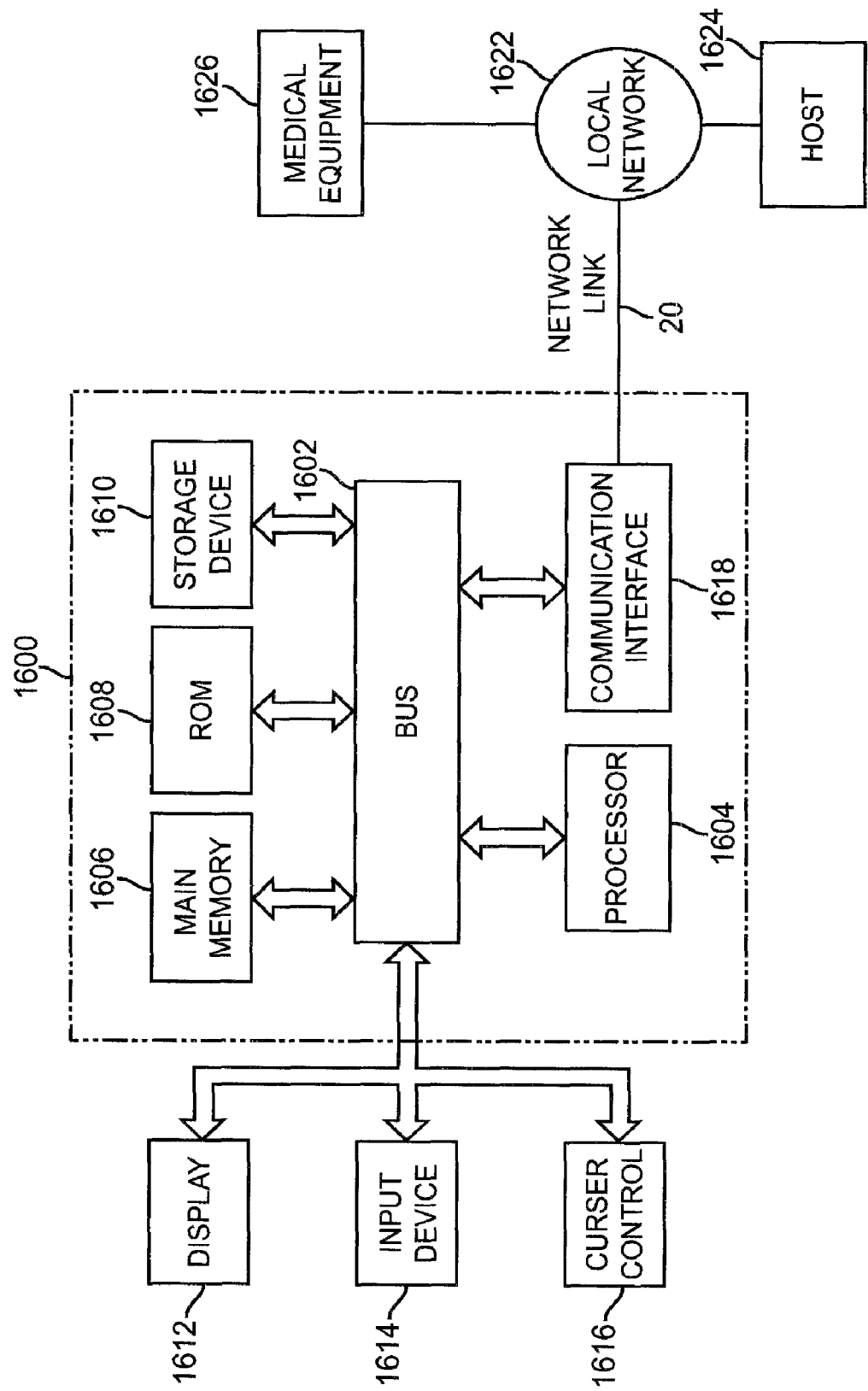
FIG. 16 illustrates a block diagram of a computer system with which embodiments described herein may be implemented.

FIG. 16 is a block diagram illustrating an embodiment of a computer system 1600 that can be used to implement various embodiments of the method described herein. Computer system 1600 includes a bus 1602 or other communication mechanism for communicating information, and a processor 1604 coupled with the bus 1602 for processing information. The processor 1604 may be an example of the processor 54, or alternatively, an example of a component of the processor 54, of FIG. 1. The computer system 1600 also includes a main memory 1606, such as a random access memory (RAM) or other dynamic storage device, coupled to the bus 1602 for storing information and instructions to be executed by the processor 1604. The main memory 1606 also may be used for storing temporary variables or other intermediate information during execution of instructions to be executed by the processor 1604. The computer system 1600 further includes a read only memory (ROM) 1608 or other static storage device coupled to the bus 1602 for storing static information and instructions for the processor 1604. A data storage device 1610, such as a magnetic disk or optical disk, is provided and coupled to the bus 1602 for storing information and instructions.

The computer system 1600 may be coupled via the bus 1602 to a display 167, such as a cathode ray tube (CRT), for displaying information to a user. An input device 1614, including alphanumeric and other keys, is coupled to the bus 1602 for communicating information and command selections to processor 1604. Another type of user input device is cursor control 1616, such as a mouse, a trackball, or cursor direction keys for communicating direction information and command selections to processor 1604 and for controlling cursor movement on display 167. This input device typically has two degrees of freedom in two axes, a first axis (e.g., x) and a second axis (e.g., y), that allows the device to specify positions in a plane.

In some embodiments, the computer system 1600 can be used to perform various functions described herein. According to some embodiments of the invention, such use is provided by computer system 1600 in response to processor 1604 executing one or more sequences of one or more instructions contained in the main memory 1606. Those skilled in the art will know how to prepare such instructions based on the functions and methods described herein. Such instructions may be read into the main memory 1606 from another computer-readable medium, such as storage device 1610. Execution of the sequences of instructions contained in the main memory 1606 causes the processor 1604 to perform the process steps described herein. One or more processors in a multi-processing arrangement may also be employed to execute the sequences of instructions contained in the main memory 1606. In alternative embodiments, hard-wired circuitry may be used in place of or in combination with software instructions to implement the invention. Thus, embodiments of the invention are not limited to any specific combination of hardware circuitry and software.

The term "computer-readable medium" as used herein refers to any medium that participates in providing instructions to the processor 1604 for execution. Such a medium may take many forms, including but not limited to, non-volatile media, volatile media, and transmission media. Non-volatile media includes, for example, optical or magnetic disks, such as the storage device 1610. Volatile media includes dynamic memory, such as the main memory 1606. Transmission media includes coaxial cables, copper wire and fiber optics, including the wires that comprise the bus 1602. Transmission media can also take the form of acoustic or light waves, such as those generated during radio wave and infrared data communications.

Common forms of computer-readable media include, for example, a floppy disk, a flexible disk, hard disk, magnetic tape, or any other magnetic medium, a CD-ROM, any other optical medium, punch cards, paper tape, any other physical medium with patterns of holes, a RAM, a PROM, and EPROM, a FLASH-EPROM, any other memory chip or cartridge, a carrier wave as described hereinafter, or any other medium from which a computer can read.

Various forms of computer-readable media may be involved in carrying one or more sequences of one or more instructions to the processor 1604 for execution. For example, the instructions may initially be carried on a magnetic disk of a remote computer. The remote computer can load the instructions into its dynamic memory and send the instructions over a telephone line using a modem. A modem local to the computer system 1600 can receive the data on the telephone line and use an infrared transmitter to convert the data to an infrared signal. An infrared detector coupled to the bus 1602 can receive the data carried in the infrared signal and place the data on the bus 1602. The bus 1602 carries the data to the main memory 1606, from which the processor 1604 retrieves and executes the instructions. The instructions received by the main memory 1606 may optionally be stored on the storage device 1610 either before or after execution by the processor 1604.

The computer system 1600 also includes a communication interface 1618 coupled to the bus 1602. The communication interface 1618 provides a two-way data communication coupling to a network link 1620 that is connected to a local network 1622. For example, the communication interface 1618 may be an integrated services digital network (ISDN) card or a modem to provide a data communication connection to a corresponding type of telephone line. As another example, the communication interface 1618 may be a local area network (LAN) card to provide a data communication connection to a compatible LAN. Wireless links may also be implemented. In any such implementation, the communication interface 1618 sends and receives electrical, electromagnetic or optical signals that carry data streams representing various types of information.

The network link 1620 typically provides data communication through one or more networks to other devices. For example, the network link 1620 may provide a connection through local network 1622 to a host computer 1624 or to equipment 1626 such as a radiation beam source or a switch operatively coupled to a radiation beam source. The data streams transported over the network link 1620 can comprise electrical, electromagnetic or optical signals. The signals through the various networks and the signals on the network link 1620 and through the communication interface 1618, which carry data to and from the computer system 1600, are exemplary forms of carrier waves transporting the information. The computer system 1600 can send messages and receive data, including program code, through the network(s), the network link 1620, and the communication interface 1618.

Although the embodiments of the systems and methods have been described with reference to CT imaging devices, it should be understood that techniques similar to those described herein may also be implemented to calibrate other types of imaging or optical devices, such as a laminar tomography machine, a MRI machine, a C-arm based x-ray imaging machine, a three dimensional angiography machine, a PET machine, or a treatment machine that is capable of generating images (such as a radiation treatment machine that includes a detector). Also, in other embodiments, any of the devices and/or methods described herein can be used to calibrate non-imaging devices, such as a positioner or a treatment machine that has no imaging capability. In further embodiments, any of the devices and/or methods described herein can be used to calibrate a machine that has a plurality of radiation sources. For example, the machine can have a first radiation source for delivering diagnostic radiation (e.g., radiation having an energy level in the kilo-electron-volt range), and a second radiation source for delivering treatment radiation (e.g., radiation having an energy level in the mega-electron-volt range). As another example, the machine can also have a plurality of diagnostic radiation sources and/or one or more treatment radiation sources.

Although particular embodiments of the present inventions have been shown and described, it will be understood that it is not intended to limit the present inventions to the preferred embodiments, and it will be obvious to those skilled in the art that various changes and modifications may be made without departing from the spirit and scope of the present inventions. For example, the term "image" as used in this specification includes image data that may be stored in a circuitry or a computer-readable medium, and should not be limited to image data that is displayed visually. The specification and drawings are, accordingly, to be regarded in an illustrative rather than restrictive sense. The present inventions are intended to cover alternatives, modifications, and equivalents, which may be included within the spirit and scope of the present inventions as defined by the claims.

What is claimed:

1. A method of determining a geometric parameter of a machine, comprising:
    using the machine to obtain an image of at least a portion of a structure, the structure having a plurality of markers, wherein the markers have predetermined position(s) relative to each other;
    determining a position of the structure based on a pattern of the markers in the image; and
    determining a geometric parameter of the machine based at least in part on the determined position of the structure.

2. The method of claim 1, wherein the machine comprises a CT imaging machine.

3. The method of claim 1, wherein the geometric parameter is selected from the group consisting of a source-to-imager distance, a source-to-axis distance, an axis of rotation, an isocenter, and a piercing point.

4. The method of claim 1, wherein the structure comprises at least four markers.

5. The method of claim 1, wherein the position of the structure is determined relative to a reference frame of the machine.

6. The method of claim 1, wherein the geometric parameter of the machine is for use in an operation of the machine.

7. A method of determining a geometric parameter of a machine, comprising:
    using the machine to obtain an image of at least a portion of a structure, the structure having a plurality of markers, wherein the markers have predetermined position(s) relative to each other;
    determining a position of the structure based on a pattern of the markers in the image; and
    determining a geometric parameter of the machine based at least in part on the determined position of the structure;
    wherein the obtained image contains a subset of the plurality of markers, and the position of the structure is determined based on a pattern of the subset of markers in the image.

8. A method of determining a geometric parameter of a machine, comprising:
    using the machine to obtain an image of at least a portion of a structure, the structure having a plurality of markers, wherein the markers have predetermined position(s) relative to each other;
    determining a position of the structure based on a pattern of the markers in the image; and
    determining a geometric parameter of the machine based at least in part on the determined position of the structure;
    wherein the step of determining the position of the structure comprises:
    estimating a position of the structure;
    calculating projected marker positions that correspond with the estimated position of the structure;
    comparing the projected marker positions with the positions of the markers obtained from the image; and
    adjusting the estimated position based on a result from the step of comparing.

9. The method of claim 8, wherein the adjusting is performed using a Gauss method by computing an inverse Jacobian matrix of marker positions.

10. A method of determining a geometric parameter of a machine, comprising:
    using the machine to obtain an image of at least a portion of a structure, the structure having a plurality of markers, wherein the markers have predetermined position(s) relative to each other;

determining a position of the structure based on a pattern of the markers in the image; and determining a geometric parameter of the machine based at least in part on the determined position of the structure;

wherein the machine is configured to obtain images in a half-fan configuration.

11. A method of determining a geometric parameter of a machine, comprising:

using the machine to obtain an image of at least a portion of a structure, the structure having a plurality of markers, wherein the markers have predetermined position(s) relative to each other;

determining a position of the structure based on a pattern of the markers in the image; and determining a geometric parameter of the machine based at least in part on the determined position of the structure;

wherein the machine comprises a first source for providing diagnostic energy, and a second source for providing treatment energy.

12. A method of determining a geometric parameter of a machine, comprising:

using the machine to obtain an image of at least a portion of a structure, the structure having a plurality of markers, wherein the markers have predetermined position(s) relative to each other;

determining a position of the structure based on a pattern of the markers in the image; and determining a geometric parameter of the machine based at least in part on the determined position of the structure;

wherein the machine comprises a plurality of radiation sources.

13. A system for determining a geometric parameter of a machine, comprising:

a processor configured to receive an image of at least a portion of a structure, the structure having a plurality of markers, wherein the markers have predetermined position(s) relative to each other;

wherein the processor is further configured to determine a position of the structure based on a pattern of the markers in the image, and determine a geometric parameter of the machine based at least in part on the determined position of the structure.

14. The system of claim 13, wherein the geometric parameter of the machine is for use in an operation of the machine.

15. A computer program product including a non-transitory medium useable by a processor, the medium having a set of instructions, an execution of which causes a process to be performed, wherein the medium comprises a volatile or non-volatile medium, the process comprising:

receiving an image of at least a portion of a structure, the structure having a plurality of markers, wherein the markers have predetermined position(s) relative to each other;

determining a position of the structure based on a pattern of the markers in the image;

determining a geometric parameter of a machine based at least in part on the determined position of the structure; and storing the determined geometric parameter.

16. The computer program product of claim 15, wherein the geometric parameter of the machine is for use in an operation of the machine.

17. A method of determining a geometric parameter of a machine, comprising:

using the machine to obtain images of at least a portion of a structure at a plurality of gantry angles;

determining positions of the structure relative to a reference frame of the machine based on the obtained images at the plurality of gantry angles;

determining a first point on the structure;

determining a second point on the structure; and determining an axis of rotation in a three-dimensional space based at least in part on the determined first and second points on the structure.

18. The method of claim 17, wherein the machine comprises a CT imaging machine.

19. The method of claim 17, wherein the machine is configured to obtain images in a half-fan configuration.

20. The method of claim 17, wherein the machine comprises a first source for providing diagnostic energy, and a second source for providing treatment energy.

21. The method of claim 17, wherein the machine comprises a plurality of radiation sources.

22. The method of claim 17, wherein the axis comprises a line connecting the first and the second points.

23. The method of claim 17, wherein the first point and the second point are relatively fixed in the reference frame of the machine when compared with a majority of the rest of the points on the structure.

24. The method of claim 17, further comprising determining a rotation center based at least in part on the axis of rotation.

25. The method of claim 17, further comprising determining a piercing point based at least in part on the determined axis of rotation.

26. The method of claim 25, wherein the step of determining the piercing point comprises:

determining a line that is perpendicular to the axis of rotation, the line having a point that coincides with a radiation source; and determining a point of intersection between the determined line and a plane associated with an imager.

27. A system for determining a geometric parameter of a machine, comprising:

a processor configured to obtain images of at least a portion of a structure at a plurality of gantry angles;

wherein the processor is further configured to determine positions of the structure relative to a reference frame of the machine based on the obtained images at the plurality of gantry angles, determine a first point on the structure, determine a second point on the structure, and determine an axis of rotation in a three-dimensional space based at least in part on the determined first and second points on the structure.

28. A computer program product including a non-transitory medium useable by a processor, the medium having a set of instructions, an execution of which causes a process to be performed, wherein the medium comprises a volatile or non-volatile medium, the process comprising:

receiving images of at least a portion of a structure at a plurality of gantry angles;

determining positions of the structure relative to a reference frame of the machine based on the obtained images at the plurality of gantry angles;

determining a first point on the structure; determining a second point on the structure;

determining an axis of rotation in a three-dimensional space based at least in part on the determined first and second points on the structure; and storing data regarding the determined axis of rotation.

29. A method of determining a geometric parameter of a machine, comprising:

placing a filter in front of a radiation source;
using the machine to obtain a first image at a first gantry angle and a second image at a second gantry angle;
determining a first point in a first image that represents the intersection between a center line of a radiation beam generated at the first gantry angle and a plane of the first image;
determining a second point in a second image that represents the intersection between a center line of a radiation beam generated at the second gantry angle and a plane of the second image;
determining a first line that includes the first point;
determining a second line that includes the second point; and
determining a geometric parameter of the machine based at least in part on the first line and the second line.

30. The method of claim 29, wherein the geometric parameter comprises an isocenter of the machine.

31. The method of claim 30, wherein the isocenter is determined by determining an intersection point between the first and the second lines.

32. The method of claim 29, wherein the filter comprises an opening.

33. The method of claim 29, wherein the filter comprises a plurality of markers.

34. The method of claim 29, wherein the first point is determined by determining a center of an image of a filter opening.

35. The method of claim 29, wherein the first point is determined by determining a centroid of a plurality of markers as they appear in an image frame.

36. The method of claim 29, wherein the filter comprises a block that defines an opening.

37. The method of claim 36, wherein the opening has a shape of a circle.

38. A system for determining a geometric parameter of a machine, comprising:
a filter configured to be secured in front of a radiation source; and
a processor, wherein the processor is configured to obtain a first image at a first gantry angle and a second image at a second gantry angle, wherein the first and the second images are generated using the machine,
determine a first point in a first image that represents the intersection between a center line of a radiation beam at the first gantry angle and a plane of the first image,
determine a second point in a second image that represents the intersection between a center line of a radiation beam at the second gantry angle and a plane of the second image,
determine a first line that includes the first point,
determining a second line that includes the second point, and
determine a geometric parameter of the machine based at least in part on the first line and the second line.

39. The system of claim 38, wherein the filter comprises a block that defines an opening.

40. The system of claim 39, wherein the opening has a shape of a circle.

41. A computer product including a non-transitory medium useable by a processor, the medium having a set of instructions, an execution of which causes a process to be performed, wherein the medium comprises a volatile or non-volatile medium, the process comprising:
obtaining a first image at a first gantry angle and a second image at a second gantry angle, wherein the first and the second images are generated using a radiation source and a filter placed in front of the radiation source;
determining a first point in a first image that represents the intersection between a center line of a radiation beam at the first gantry angle and a plane of the first image;
determining a second point in a second image that represents the intersection between a center line of a radiation beam at the second gantry angle and a plane of the second image;
determining a first line that includes the first point;
determining a second line that includes the second point;
determining a geometric parameter of the machine based at least in part on the first line and the second line; and
storing the determined geometric parameter.

42. The computer product of claim 41, wherein the filter comprises a block that defines an opening.

43. The computer product of claim 42, wherein the opening has a shape of a circle.

44. A method for use to determine a geometric parameter of a machine, comprising:
verifying an isocenter of a machine using a processor;
wherein the act of verifying the isocenter is performed without a need to place a marker at the isocenter of the machine.

45. The method of claim 44, wherein the verifying comprises:
determining a position of a calibration device;
determining a point that coincides with an expected position of the isocenter of the machine based on the position of the calibration device; and
determining whether the point coincides with an intersection point between a first radiation beam generated at a first gantry angle and a second radiation beam generated at a second gantry angle.

46. The method of claim 45, wherein the determining whether the point coincides with the intersection point comprises:
generating a first image at the first gantry angle and a second image at the second gantry angle;
determining a first point in the first image that represents a projection of a center point of a radiation source at the first gantry angle;
determining a second point in the second image that represents a projection of the center point of the radiation source at the second gantry angle;
projecting the point onto the first and second images;
comparing the projected point with the first point; and
comparing the projected point with the second point.

47. The method of claim 44, wherein the isocenter comprises an expected isocenter.

48. A system for use in a process to determine a geometric parameter of an imaging device, comprising:
a structure having a three-dimensional configuration; and
a plurality of markers secured to the structure;
wherein the plurality of markers are positioned relative to each other such that their positions collectively form an irregular pattern, and wherein the plurality of markers collectively occupies a three-dimensional space.

49. The system of claim 48, wherein the plurality of markers have a same size.

* * * * *